US010155040B2

(12) United States Patent
Newton et al.

(10) Patent No.: US 10,155,040 B2
(45) Date of Patent: Dec. 18, 2018

(54) MIXED METAL COMPOUNDS FOR TREATMENT OF HYPERPHOSPHATAEMIA

(75) Inventors: Maurice Sydney Newton, Sandbacj (GB); Alexis John Toft, Warrington (GB); Nigel Peter Rhodes, Warrington (GB)

(73) Assignee: OPKO IRELAND GLOBAL HOLDINGS, LTD., Grand Cayman (KY)

( * ) Notice: Subject to any disclaimer, the term of this patent is extended or adjusted under 35 U.S.C. 154(b) by 788 days.

(21) Appl. No.: 12/738,293

(22) PCT Filed: Oct. 15, 2008

(86) PCT No.: PCT/GB2008/003509
§ 371 (c)(1),
(2), (4) Date: Apr. 16, 2010

(87) PCT Pub. No.: WO2009/050468
PCT Pub. Date: Apr. 23, 2009

(65) Prior Publication Data
US 2010/0215770 A1 Aug. 26, 2010

(30) Foreign Application Priority Data
Oct. 16, 2007 (GB) .................. 0720220.3

(51) Int. Cl.
*A61K 33/26* (2006.01)
*A61K 45/06* (2006.01)
*A61K 9/20* (2006.01)
*A61K 9/28* (2006.01)
*A61K 33/06* (2006.01)
*A61K 33/10* (2006.01)
*A61K 33/24* (2006.01)
*A61K 33/30* (2006.01)
*A61K 33/32* (2006.01)
*A61K 33/34* (2006.01)
*C01F 7/00* (2006.01)
*C01G 49/00* (2006.01)
*C01G 49/02* (2006.01)

(52) U.S. Cl.
CPC ............ *A61K 45/06* (2013.01); *A61K 9/2027* (2013.01); *A61K 9/2059* (2013.01); *A61K 9/2846* (2013.01); *A61K 33/06* (2013.01); *A61K 33/10* (2013.01); *A61K 33/24* (2013.01); *A61K 33/26* (2013.01); *A61K 33/30* (2013.01); *A61K 33/32* (2013.01); *A61K 33/34* (2013.01); *C01F 7/005* (2013.01); *C01G 49/009* (2013.01); *C01G 49/02* (2013.01); *C01P 2002/22* (2013.01); *C01P 2002/72* (2013.01); *C01P 2004/61* (2013.01); *C01P 2006/12* (2013.01)

(58) Field of Classification Search
None
See application file for complete search history.

(56) References Cited

U.S. PATENT DOCUMENTS

| 2,222,924 | A | 11/1940 | Weiss |
| 2,812,344 | A | 11/1957 | Oroshnik |
| 3,101,270 | A | 8/1963 | Evans et al. |
| 3,395,211 | A | 7/1968 | Wielich |
| 3,650,704 | A | 3/1972 | Kumura et al. |
| 3,743,098 | A | 7/1973 | Martinez |
| 3,796,792 | A | 3/1974 | Miyata et al. |
| 3,879,523 | A | 4/1975 | Miyata et al. |
| 3,984,392 | A | 10/1976 | van der Veen et al. |
| 4,192,900 | A | 3/1980 | Cheng |
| 4,254,099 | A | 3/1981 | Asmussen et al. |
| 4,351,814 | A | 9/1982 | Miyata et al. |
| 4,370,280 | A | 1/1983 | Oediger et al. |
| 4,415,555 | A | 11/1983 | Anabuki et al. |
| 4,458,026 | A | 7/1984 | Reichle |
| 4,514,389 | A | 4/1985 | Miyata |
| 4,566,986 | A | 1/1986 | Waldmann |
| 4,582,705 | A | 4/1986 | Primes et al. |
| 4,609,543 | A | 9/1986 | Morris et al. |
| 4,629,626 | A | 12/1986 | Miyata et al. |
| 4,661,330 | A | 4/1987 | Chane-Ching et al. |
| 4,689,219 | A | 8/1987 | Sugden |
| 4,735,629 | A | 4/1988 | Glemser et al. |
| 4,786,510 | A | 11/1988 | Nakel et al. |
| 4,801,454 | A | 1/1989 | Coveney |
| 4,970,079 | A | 11/1990 | Hem et al. |
| 4,994,283 | A | 2/1991 | Mehansho et al. |
| 5,002,747 | A | 3/1991 | Le Loarer |

(Continued)

FOREIGN PATENT DOCUMENTS

CA 1198674 A1 12/1985
DE 2061136 A1 7/1971
(Continued)

OTHER PUBLICATIONS

Sigma-Aldrich® product information for Iron(III) nitrate nonanhydrate, retrieved from <www.sigmaaldrich.com> on Jun. 11, 2012, p. 1.*
(Continued)

*Primary Examiner* — David J Blanchard
*Assistant Examiner* — Ivan A Greene
(74) *Attorney, Agent, or Firm* — Marshall, Gerstein & Borun LLP

(57) ABSTRACT

The present invention relates to mixed metal compounds having pharmaceutical activity, especially as phosphate binders. It also extends to methods of manufacture of those compounds, as well as to pharmaceutical compositions containing such compounds. It further relates to their pharmaceutical use. In particular, the present invention relates to use of compounds of Formula (I): $M^{II}_{1-a}M^{III}_{a}$ wherein M" is at least one bivalent metal (i.e. with two positive charges); M1 is at least one trivalent metal (i.e. with three positive charges); and $1 > a > 0.4$.

76 Claims, 2 Drawing Sheets

(56) References Cited

U.S. PATENT DOCUMENTS

Figure 1:
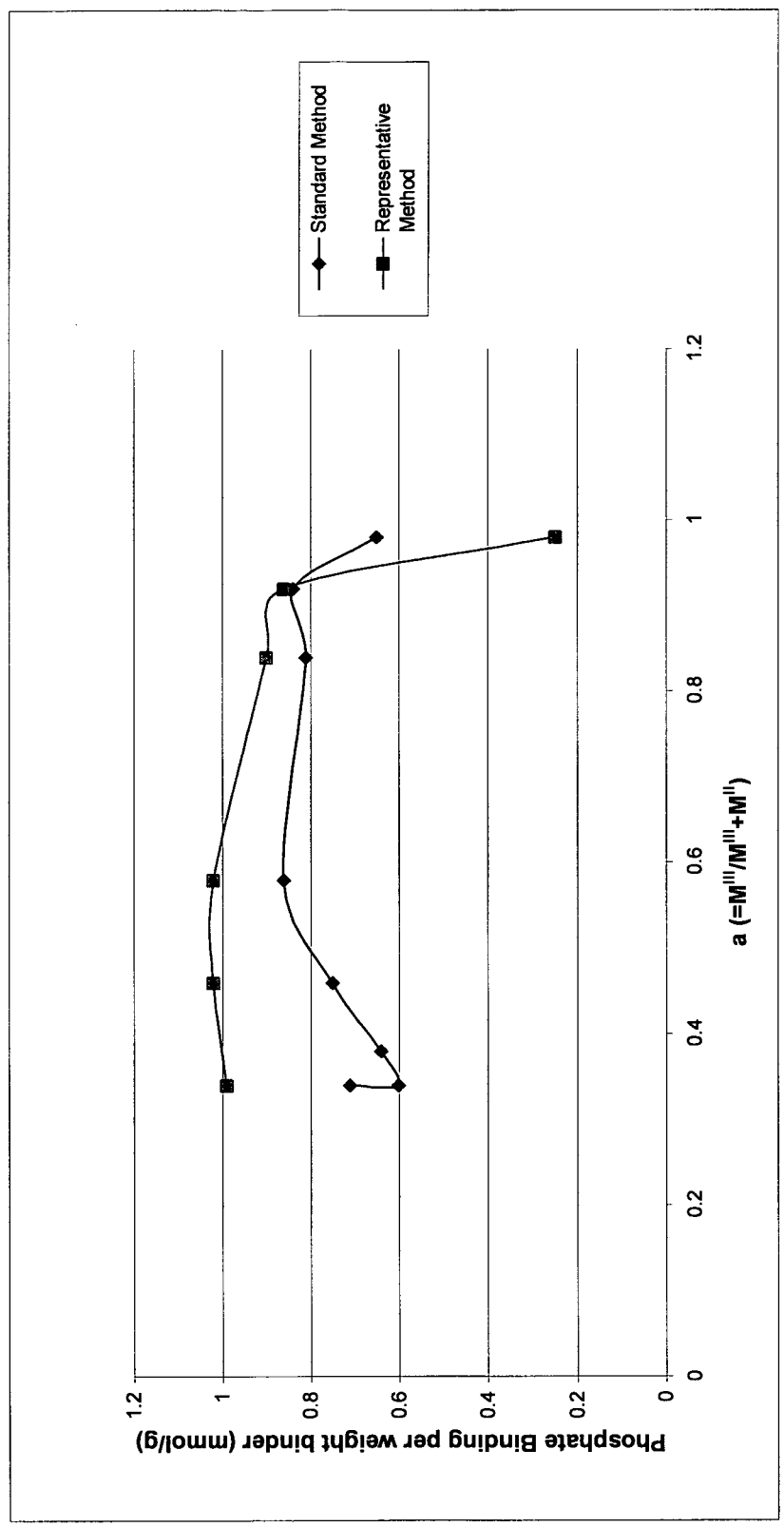

| | | |
|---|---|---|
| 5,085,869 A | 2/1992 | Olthoff et al. |
| 5,112,604 A | 5/1992 | Beaurline et al. |
| 5,153,156 A | 10/1992 | Schutz et al. |
| 5,173,284 A | 12/1992 | Moisset et al. |
| 5,185,093 A | 2/1993 | Ichikawa et al. |
| 5,213,794 A | 5/1993 | Fritsch et al. |
| 5,246,899 A | 9/1993 | Bhattacharyya |
| 5,273,767 A | 12/1993 | Burgum |
| 5,300,302 A | 4/1994 | Tachon et al. |
| 5,506,248 A | 4/1996 | Nikfar et al. |
| 5,514,281 A | 5/1996 | Boos et al. |
| 5,525,305 A | 6/1996 | Minekus et al. |
| 5,571,336 A | 11/1996 | Wurzburger et al. |
| 5,651,997 A | 7/1997 | Makino et al. |
| 5,654,011 A | 8/1997 | Jackson et al. |
| 5,656,080 A | 8/1997 | Staniforth et al. |
| 5,817,340 A | 10/1998 | Roche et al. |
| 5,846,426 A | 12/1998 | Boos et al. |
| 5,968,976 A | 10/1999 | Murrer et al. |
| 6,028,023 A | 2/2000 | Vierheilig |
| 6,039,981 A | 3/2000 | Woo et al. |
| 6,103,126 A | 8/2000 | Boos et al. |
| 6,174,442 B1 | 1/2001 | Geisser et al. |
| 6,287,596 B1 | 9/2001 | Murakami et al. |
| 6,448,323 B1 | 9/2002 | Jordan et al. |
| 6,576,255 B1 | 6/2003 | Petereit et al. |
| 6,576,665 B2 | 6/2003 | Dennett, Jr. et al. |
| 6,596,311 B1 | 7/2003 | Dobetti |
| 6,696,087 B2 | 2/2004 | Matsuda et al. |
| 6,720,005 B1 | 4/2004 | Ayres |
| 6,733,780 B1 | 5/2004 | Tyler et al. |
| 6,749,864 B2 | 6/2004 | Makino et al. |
| 6,790,895 B2 | 9/2004 | Stelandre et al. |
| 6,794,367 B1 | 9/2004 | Tanida et al. |
| 6,926,912 B1 | 8/2005 | Roberts et al. |
| 7,259,192 B2 | 8/2007 | Liu et al. |
| 7,300,670 B2 | 11/2007 | Venus et al. |
| 7,799,351 B2 | 9/2010 | Roberts et al. |
| 2002/0122786 A1 | 9/2002 | Matsuda et al. |
| 2003/0150249 A1 | 8/2003 | Gillman et al. |
| 2003/0185886 A1 | 10/2003 | Lee et al. |
| 2004/0022872 A1 | 2/2004 | Sofue et al. |
| 2004/0105896 A1 | 6/2004 | Roberts et al. |
| 2004/0247696 A1 | 12/2004 | Antelman |
| 2005/0260271 A1 | 11/2005 | Bringley |
| 2005/0266071 A1 | 12/2005 | Olmstead et al. |
| 2006/0177415 A1 | 8/2006 | Burke |
| 2008/0187602 A1 | 8/2008 | Ferdinando et al. |
| 2009/0175959 A1 | 7/2009 | Bando et al. |
| 2009/0317459 A1 | 12/2009 | Pennel et al. |
| 2010/0215770 A1 | 8/2010 | Newton et al. |
| 2011/0014301 A1 | 1/2011 | Roberts et al. |
| 2012/0093943 A1 | 4/2012 | Newton et al. |
| 2012/0201864 A1 | 8/2012 | Applewhite et al. |
| 2013/0323325 A1 | 12/2013 | Applewhite et al. |

FOREIGN PATENT DOCUMENTS

| | | |
|---|---|---|
| DE | 3346943 A1 | 7/1985 |
| DE | 3402878 A1 | 8/1985 |
| DE | 3801382 A1 | 8/1989 |
| EP | 0050792 A1 | 5/1982 |
| EP | 0134936 A1 | 3/1985 |
| EP | 0146410 A2 | 6/1985 |
| EP | 0150792 A2 | 8/1985 |
| EP | 0368420 A2 | 5/1990 |
| EP | 0577294 A2 | 1/1994 |
| EP | 0638313 A1 | 2/1995 |
| EP | 1304104 A2 | 4/2003 |
| EP | 1413197 A2 | 4/2004 |
| EP | 1707178 A1 | 10/2006 |
| EP | 1932808 A1 | 6/2008 |
| EP | 1946750 A1 | 7/2008 |
| ES | 2018952 A6 | 5/1991 |
| FR | 1214473 A | 4/1960 |
| FR | 2254556 A1 | 7/1975 |
| GB | 1336866 | * 11/1973 |
| GB | 2031395 A | 4/1980 |
| GB | 2254556 A | 10/1992 |
| HU | 173556 B | 6/1979 |
| HU | 201880 B | 1/1991 |
| IE | 63343 B1 | 4/1995 |
| IN | 192168 A1 | 3/2004 |
| JP | 61036222 A | 2/1986 |
| JP | 62145024 A | 6/1987 |
| JP | 05155776 A | 6/1993 |
| JP | 05208816 A | 8/1993 |
| JP | 10059842 A | 3/1998 |
| JP | 10101569 A | 4/1998 |
| JP | 10236960 A | 9/1998 |
| JP | 3001114 B2 | 1/2000 |
| JP | 2000086537 A | 3/2000 |
| JP | 2001517633 A | 10/2001 |
| JP | 2004089760 A | 3/2004 |
| PL | 189716 B1 | 6/1997 |
| PL | 200957 B1 | 11/1999 |
| SU | 414849 A1 | 9/1977 |
| WO | WO-91/18835 A1 | 12/1991 |
| WO | 9201458 | 2/1992 |
| WO | WO 9201458 | * 2/1992 |
| WO | WO 9201458 A1 | * 2/1992 |
| WO | WO-93/22237 A1 | 11/1993 |
| WO | WO-94/09798 A1 | 5/1994 |
| WO | WO-95/11033 A1 | 4/1995 |
| WO | WO-95/29679 A1 | 11/1995 |
| WO | WO-96/30029 A1 | 10/1996 |
| WO | WO-97/11166 A1 | 3/1997 |
| WO | WO-97/22266 A1 | 6/1997 |
| WO | WO-97/48380 A1 | 12/1997 |
| WO | 9915189 | 4/1999 |
| WO | WO-99/44580 A1 | 9/1999 |
| WO | WO-00/32189 A1 | 6/2000 |
| WO | WO-01/27069 A1 | 4/2001 |
| WO | WO-01/049301 A1 | 7/2001 |
| WO | WO-03/013473 A1 | 2/2003 |
| WO | WO-03/017980 A1 | 3/2003 |
| WO | WO-03/028706 A1 | 4/2003 |
| WO | WO-03/072084 A1 | 9/2003 |
| WO | WO-03/092658 A1 | 11/2003 |
| WO | WO-2004/016553 A2 | 2/2004 |
| WO | WO-2004/018094 A1 | 3/2004 |
| WO | WO-2005/009381 A2 | 2/2005 |
| WO | WO-2005/012194 A1 | 2/2005 |
| WO | WO-2005/018651 A1 | 3/2005 |
| WO | WO-2005/027876 A1 | 3/2005 |
| WO | 2006085079 A2 | 8/2006 |
| WO | WO 2006085079 A2 * 8/2006 ............ A61K 33/24 |
| WO | WO-2007/074909 A1 | 7/2007 |
| WO | 2007088343 A2 | 8/2007 |
| WO | WO-2007/135362 A2 | 11/2007 |
| WO | 2008071747 A1 | 6/2008 |
| WO | WO-2008/129034 A1 | 10/2008 |
| WO | WO-2009/016349 A1 | 2/2009 |
| WO | WO-2009/050468 A1 | 4/2009 |

OTHER PUBLICATIONS

Kostura B. et al., "Rehydration of calcined Mg-Al hydrotalcite in acidified chloride-containing aqueous solution,", Collection of Czechoslovak Chemical Communications, 2007, vol. 72, No. 9, p. 1284-1294. XP002508564.*

Abramowitz et al., Serum alkaline phosphatase and phosphate and risk of mortality and hospitalization, Clin. J. Am. Soc. Nephrol., 1:1064-71 (2010).

Ambrogi et al., Intercalation compounds of hydrotalcite-like anionic clays with anti-inflammatory agents, II: Uptake of diclofenac for a controlled release formulation, AAPS PharmSciTech., 3(3):E26 (2002), pp. 1-6.

Aoshima et al., Glycerin fatty acids esters as a new lubricant of tablets, Int. J. Pharm., 293:25-34 (2005).

Badawy et al., Effect of drug substance particle size on the characteristics of granulation manufactured in a high-shear mixer, AAPS PharmSciTech., 1(4):E33 (2000), pp. 55-61.

(56) References Cited

OTHER PUBLICATIONS

Badreddine et al.,Ion exchange of different phosphate ions into the zinc-aluminium-chloride layered double hydroxide, Materials Lett., 38(6): 391-5 (1999).
Barriga et al., Hydrotalcites as sorbent for 2,4,6-trinitrophenol: influence of the layer composition and interlayer anion, J. Mater. Chem., 12:1027-34 (2002).
Bolhuis et al., Interaction of tablet disintegrants and magnesium strearate during mixing I: effect on tablet disintegration, J. Pharm. Sci., 70(12):1328-30 (1981).
Bolognini et al., Mg/Al mixed oxides prepared by coprecipitation and sol-gel routes: a comparison of their physico-chemical features and performances in m-cresol methylation, Microporous and Mesoporous Materials, 66:77-89 (2003).
Bothwell, Overview and mechanisms of iron regulation, Nutrition Rev., 53:237-45 (Sep. 1995).
Brouwers et al., Biopharmaceutical tests on antacids: in vitro and in vivo studies, Drugs Under Experiment. Clin. Res., 5:55-61 (1997).
Brouwers et al., De invioed van de toedieningsvorm op de weringsduur en op het pH-Bereik bij antacida: een in-vitro en in-vivo studie, Pharmaceutisch Weekblad, 111:1244-8 (1976) (abstract only).
Brouwers, Liquid Antacids, Pharmaceutisch Weekblad, 110:337-51 (1975) (abstract only).
Budavari et al. (eds.), *The Merck Index*, pp. 277, 331, and 917, Merck & Co. (1996).
Carlino, Chemistry between the sheets, Chemistry in Britain, pp. 59-62 (Sep. 1997).
Chatelet et al., Competition between monovalent and divalent anions for calcined and uncalcined hydrotalcite: anion exchange and adsorption sites, Colloids and Surfaces A: Physiochemical and Engineering Aspects, 111:167-75 (1996).
Chitrakar et al., Adsorption of phosphate from seawater on calcined MgMn-layered double hydroxides, J. Colloid Interface Sci., 290(1): 45-51 (2005).
Cook, Adaptation in iron metabolism, Am. J. Clin. Nutr., 51(2):301-8 (1990).
De Roy et al., Antionic Clays: Trends in Pillaring Chemistry, chapter 7, pp. 108-169 In: *Synthesis of Microporous Materials* (1992).
De Roy et al., Layered double hydroxides: synthesis and post-synthesis modification, Chapter I (entire) incl. pp. 33-34, In: Rives (ed.), *Layered Double Hydroxides: Present and Future*, Nova Science Publishers, Inc. (2001).
De Roy et al., Surface Text and Electron Microscopy Studies, pp. 243-244 In: Rives (ed.), *Layered Double Hydroxides: Present and Future*, Nova Science Publishers, Inc. (2001).
Del Arco et al., Effect of the Mg:Al ratio on borate (or silicate)/nitrate exchange in hydrotalcite, J. Solid State Chem., 151(2):272-80 (2000).
Del Arco et al., Surface and textural properties of hydrotalcite-like materials and their decomposition products, In: Rouquerol et al. (eds.), *Characterization of Porous Solids III, Studies in Surface Science and Catalysis*, vol. 87, pp. 507-515 (1994).
Emmett, A comparison of clinically useful phosphorus binders for patients with chronic kidney failure, Kidney Int.,66:S25-S32 (2004).
Erickson et al., A study of structural memory effects in synthetic hydrotalcites using environmental SEM, Materials Lett., 59:226-9 (2005).
Evans et al., Structural Aspects of Layered Double Hydroxides pp. 1-12, In: Duan et al. (eds.), *Layered Double Hydroxides*, vol. 119, Springer (2006).
Ferreira et al., Thermal decomposition and structural reconstruction effect on Mg Fe based hydrocalcite compounds, J. Solid State Chem., 177:3058-69 (2004).
Frost et al., Thermal decomposition of synthetic hydrotalcites reevesite and pyroaurite, J. Therm. Analysis Calorimetry, 76:217-25 (2004).
Grant et al. (eds.), *Grant & Hackh's Chemical Dictionary*, 5th ed., McGraw Hill, pp. 571 (1987).

Grubel et al., Interaction of an aluminum-magnesium containing antacid and gastric mucus: possible contribution to the cytoprotective function of antacids, Aliment. Pharmacol. Ther., 11(1):139-45 (1997).
Guillot et al., The use of magnesium-containing phosphate binders in patients with end-stage renal disease on maintenance hemodialysis, Nephron., 30(2): (1982), pp. 114-117.
Hansen et al., Formation of synthetic analogues of double metal-hydroxy carbonate minerals under controlled pH conditions: I. The synthesis of pyroaurite and reevesite, Clay Minerals, 25:161-79 (1990).
Hansen et al., Synthesis and characterization of pyroaurite, Appl. Clay Sci., 10(1-2):5-19 (1995).
Hansen et al., The use of glycerol intercalates in the exchange of $CO_3^{2-}$ with $SO_4^{2-}$, $NO^{3-}$ or $C_L$ in pyroaurite-type compounds, Clay Minerals, 26:311-27 (1991).
Hashi et al., Preparation and properties of pyroaurite-like hydroxy minerals, Clays and Clay Minerals, 31(2):152-4 (1983).
Hibino et al., Calcination and rehydration behavior of Mg—Fe—CO3 hydrotalcite-like compounds, J. Materials Sci. Lett., 19(16):1403-5 (2000).
Hirahara et al., Synthesis and antacid property of Mg—Fe layered double hydroxide, Nendo Kagaku—J. Clay Sci. Soc. of Japan, 42(2):70-6 (2002).
International Specialty Products, Pharmaceuticals Solid Dosage Forms (2004), pp. 1-13.
Iranloye et al., Effects of compression force, particle size and lubricants on dissolution rate, J. Pharm. Sci., 67(4):535-9 (1978).
Ishimura et al., Hyper- and Hypophosphataemia pp. 149-158, In: Morii et al. (eds.), *Calcium in Internal Medicine*, Springer (2002).
Kaplan et al., A preference study: calcium acetate tablets versus gelcaps in hemodialysis patients, Nephrol. Nurs. J., 29(4):363-5 (2002).
Kokot et al., A rotating disk study on the rates of hydrotalcite dissolution at 25° C., Pharmazie, 48 (H4):287-9 (1993).
Konorev et al., Selection of the optimal antacid drug in clinical practice, Consilium Medicum, vol. 5, issue 10 (2003), pp. 1-10.
Kovanda et al., Thermal behavior of Ni—Mn layered double hydroxide and characterization of formed oxides, Solid State Sci., 5:1019-26 (2003).
Labajos et al., New layered double hydroxides with hydrotalcite structure containing Ni(II) and V(III), J. Materials Chem., 9:1033-9 (1999).
Larsson et al., Estimation of the bioavailability of iron and phosphorous in cereals using a dynamic in vitro gastrointestinal model, J. Sci. Food Agric., 74:99-106 (1997).
Lazaridis et al., Flotation of metal loaded clay anion exchangers, Part II: the case of arsenates, Chemosphere, 47:319-24 (2002).
Lazaridis et al., Flotation of metal loaded clay anion exchangers, Part II: the case of chromates, Chemosphere, 42:373-8 (2001).
Lazaridis, Sorption removal of anions and cations in single batch systems by uncalcined and calcined Mg—Al—CO3 hydrotalcite, Water Air Soil Pollution, 146:127-39 (2003).
Leinonen et al., Physical and lubrication properties of magnesium stearate, J. Pharm. Sci., 81(12):1194-8 (1992).
Li et al., Enteric-coated layered double hydroxides as a controlled release drug delivery system, Int. J. Pharm., 287(1-2):89-95 (2004).
Li et al., Stoichiometric Synthesis of Pure $MFe_2O_4$ (M=Mg, Co, and Ni) Spinel Ferrites from Tailored Layered Double Hydroxide (Hydrotalcite-Like) Precursors, Chem. Mater., 16(8):1597-602 (2004).
Lin et al., Evaluation of buffering capacity and acid neutralizing-pH time profile of antacids, J. Formos. Med. Assoc., 97:704-10 (1998).
Linares et al., The influence of hydrotalcite and cancrinite type zeolite in acidic aspirin solutions, Microporous and Mesoporous Materials, 74:105-10 (2004).
MacCara, Acid neutralization capacity of Canadian antacid formulations, Can. Med. Assoc. J., 132:523-7 (1985).
Marchi et al., Impregnation-induced memory effect of thermally activated layered double hydroxide, Appl. Clay Sci., 13:35-48 (1998).
McCance et al., Absorption and excretion of iron, The Lancet, pp. 680-684 (Sep. 18, 1937).

(56) References Cited

OTHER PUBLICATIONS

Meng et al., Preparation and thermal decomposition of magnesium/iron (III) layered double hydroxide intercalated by hexacyanoferrate (III) ions, J. Mater. Sci., 39:4655-7 (2004).
Meng et al., Preparation of magnetic material containing MgFe2O4 spinel ferrite from a Mg—Fe(III) layered double hydroxide intercalated by hexacyanoferrate(III) ions, Mater.Chem. Phys., 86:1-4 (2004).
*Merck Index*, p. 969, entries 5694-707. (1996).
Miederer et al., Acid neutralization and bile acid binding capacity of hydrocalcite compared with other antacids: an in-vitro study, Chinese J. Digestive Diseases, 4(3):140-6 (2003).
Miyata et al., Physiochemical properties of synthetic hydrotalcites in relation to composition, Clays and Clay Minerals, 28(1):50-6 (1980).
Murthy et al., Effect of shear mixing on in vitro drug release of capsule formulations containing lubricants, J. Pharm. Sci., 66(9):1215-9 (1977).
Naylor et al., Use of gastrointestinal model and gastroplus for the prediction of in vivo performance, Industrial Pharmacy, 12:9-12 (2006).
Newman et al., Comparative study of some layered hydroxide salts containing exchangable interlayer anions, J. Solid State Chem., 148:26-40 (1999).
O'Donovan et al., Substitution of aluminium salts by magnesium salts in control of dialysis hyperphosphataemia, The Lancet, pp. 880-881 (Apr. 19, 1986).
Oe et al., Long-term use of magnesium hydroxide as a phosphate binder in patients on hemodialysis, Clin. Nephrol., 28(4):180-5 (1987).
Pesic et al., Thermal characteristics of a synthetic hydrotalcite like material, J. Mater. Chem., 2(10): (1992), pp. 1069-1073.
Playle et al., The in-vitro antacid and anti-pepsin activity of hydrotalcite, Pharm. Acta Helv., 49(9/10:298-302 (1974).
Powell et al., The chemistry between aluminum in the gastrointestinal lumen and its uptake and absorption, Proc. Nutrition Soc., 52:241-53 (1993).
Rajamathi et al., Reversable thermal behaviour of the layered double hydroxide of Mg with Al: mechanistic studies, J. Mater. Chem., 10:2754-7 (2000).
Raki et al., Preparation, Characterization, and Moessbauer Spectroscopy of Organic Anion Intercalated Pyroaurite-like Layered Double Hydroxides, Chem. Mater., 7(1):221-4 (1995).
Remuzzi et al., Hematologic consequences of renal failure, *The Kidney*, vol. II, 5th ed. pp. (1996), pp. 2079-2102.
Rives, Study of Layered Double Hydroxides by Thermal Methods, chapter 4, pp. 116-133 In: Rives (ed.), *Layered Double Hydroxides: Present and Future*, Nova Science Pub Inc. (2001).
Robolot et al., Effect of lubricant level and applied copressional pressure on surface friction of tablets, J. Pharm. Sci., 74(6):697-9 (1985).
Rodriguez-Benot et al., Mild hyperphosphatemia and mortality in hemodialysis patients, Am. J. Kidney Dis., 46(1):68-77 (2005).
Rubinstein et al., The effect of granule size on the in vitro and in vivo properties of bendrofluazide tables 5mg, Pharm. Acta Helv., 52 (1/2): 5-10 (1977).
Rudnic et al., Oral Solid Dosage Forms, chapter 45, pp. 858-890 In: Gennaro (ed.), *Remington: The Science and Practice of Pharmacy*, 20th ed., Lippincott Williams & Wilkins (2000).
Sato et al., Adsorption of various anions by magnesium aluminum oxide Mg(0.7)Al(0.3)O(1.15), Ind. Eng. Chem. Prod. Res. Dev., 25:89-92 (1986).
Sato et al., Causticization of sodium carbonate with rock-salt-type magnesium aluminium oxide formed by the thermal decomposition of hydrotalcite-like layered double hydroxide, J. Chem. Tech. Biotechnol., 57:137-40 (1993).
Schwarz et al., Association of disorders in mineral metabolism with progression of chronic kidney disease, Clin. J. Am. Soc. Nephrol., 1:825-31 (2006).

Sheikh et al., Reducation of dietary phosphorus absorption by phosphorous binders: A theoretical, in vitro, and in vivo study, J. Clin. Invest., 83:66-73 (1989).
Spengler et al., Cross-linked iron dextran is an efficient oral phosphate binder in the rat, Nephrol. Dial. Transplant., 11(5):808-12 (1996).
Stamatakis et al., Influence of pH on in vitro disintegration of phosphate binders, Am. J. Kidney Dis., 32(5):808-12 (1998).
Suren, Evaluation of lubricants in the development of tablet formulation, Dansk TIDSskr. Farm 45, pp. 331-338 (1971).
Tezuka et al, The Synthesis and Phosphate Adsorptive Properties of Mg(II)—Mn(III) Layered Double Hydroxides and Their Heat-Treated Materials, Bull Chem. Soc. Jpn. 2004, 77:2101-7 (2004).
Tichit et al., Catalysis by hydrotalcites and related materials, Cattech, 7(6):206-17 (2003).
Trifiro et al, Hydrotalcite-like Anionic Clays (Layered Double Hydroxides), vol. 7, chapter 8, pp. 251-291, In: Alberti et al. (eds.) *Comprehensive Supramolecular Chemistry*, Pergamon, Oxford (1996).
Ulibarri et al., Kinetics of the thermal dehydration of some layered hydroxycarbonates, Thermochimica Acta, 135:231-6 (1998).
USANA Technical Bulletin, Tablet Excipients (Jun. 1999).
Van Der Voet et al., Intestinal absorption of aluminium from antacids: a comparison between hydrotalcite and algeldrate, Clin. Tech., 24(6):545-3 (1986).
Vatier et al., Antacid activity of calcium carbonate and hydrotalcite tablets, Arzneim-Forsch/Drug Res., 44(4):514-8 (1994).
Vitkova et al., The use of some hydrophobic substances in tablet technology, Milan Chilabala, Acta Pharamceutica Hungaria, 68:336-44 (1998).
Zhang et al., Phosphorous anion exchange characteristic of a pyroaurite-like compound, Inorg. Mater., 4:132-8 (1997).
Zhang et al., Synthesis and characterization of a novel nanoscale magnetic solid base catalyst involving a layered double hydroxide supported on a ferrite core, J. Solid State Chem., 177:772-80 (2004).
Zhao et al., Preparation of layered double-hydroxide nanomaterials with a uniform crystalite size using a new method involving separate nucleation and aging steps, Chem. Mater., 14(10):4286-91 (2002).
Zhu et al., Adsorption of phosphate by hydrotalcite and its calcined product, Acta Mineralogica Sinica, 25(1):27-32 (2005).
Zhu et al., Different Mg to Fe Ratios in the Mixed Metal MgFe Hydroxy-Carbonate Compounds and the Effect on Phosphate Binding Compared with Established Phosphate Binders, XP-002508562, Journal of Pharmaceutical Sciences, vol. 91, No. 01, Jan. 2002.
McIntyre C. et al., "Iron-magnesium hydroxycarbonate (alpharen): a novel non calcium containing phosphate binder for the treatment of hyperphosphataemia in chronic haemodialysis patients," Nephrology Dialysis Transplantation, 2007, vol. 22, No. suppl. 6, p. 171. XP02508563 & 44th ERA-EDTA Congress, Barcelona, Jun. 22-24, 2007.
Seida Y. et al., "Removal of humic substances by layered double hydroxide containing iron", Water Research, 2000, vol, 34, No. 5, p. 1487-1494.
Shen J. et al., "Preparation and characterization of Fe/MgO catalysts obtained from hydrotalcite-like compounds," Catalysis Today, 1996, vol. 30, p. 77-82. XP002265886.
Titulaer M. K. et al., "The formation of ice between hydrotalcite particles measured by thermoporometry," Clay Minerals, 1996, vol 31. No. 2, p. 263-277.
Das J. et al., "Adsorption of phosphate by layered double hydroxides in aqueous solutions," Applied Clay Science, 2006, vol. 32, No. 3-4, p. 252-260. XP005423758.
Autissier V. et al., Relative in vitro efficacy of the phosphate binders lanthanum carbonate and sevelamer hydrochloride, Journal of Pharmaceutical Sciences, Oct. 2007, vol. 96, No. 10, p. 2818-2827.
Adachi-Pagano M. et al., "Synthesis of Al-rich hydrotalcite-like compounds by using the urea hydrolysis reaction—control of size and morphology," Journal of Materials Chemistry, 2003, vol. 13, No. 8, p. 1988-1993. XP002508565.
Drüeke T.B., Lanthanum Carbonate as a First-Line Phosphate Binder: the "Cons", Seminars in Dialysis, Jul./Aug. 2007, vol. 20, Issue 4, p. 329-332.

(56) References Cited

OTHER PUBLICATIONS

Albaaj F. and Hutchison A. J. et al., Hyperphosphataemia in renal failure: causes, consequences and current management, Drugs, 2003, vol. 63, No. 6. p. 577-596.

Shin Hang-Sik et al., Phosphorus removal by hydrotalcite-like compounds (HTLcs), Water Science Technology, 1996, vol. 34, No. 1-2, p. 161-168.

Ookubo A. et al., Preparation and Phosphate Ion-Exchange Properties of a Hydrotalcite-like Compound, Langmuir, 1993, vol. 9, p. 1418-1422.

Ookubo A. et al., Hydrotalcites as potential adsorbents of intestinal phosphate, Journal Pharmaceutical Sciences, Nov. 1992, vol. 81, No. 11, p. 1139-1140.

Seida Y. et al., Removal of phosphate by layered double hydroxides containing iron, Water Research, 2002, vol. 36, p. 1306-1312.

The National Kidney Foundation Kidney Disease Quality Outcomes Initiative, Clinical Practice Guidelines for Bone Metabolism and Disease in Chronic Kidney Disease, 2003, Guide 5, p. 1 pt 5.5.

Zhang et al., Synthesis of Mg/Fe pyroaurite-like compounds and their anion-exchange characteristics, Inorg. Mater., 2(259):480-5 (1995).

Hollander et al., Antacids vs. placebos in peptic ulcer therapy: a controlled double-blind investigation, JAMA, 226(10):1181-5 (1973).

Hudson et al., Thermal conversion of a layered (Mg/Al) double hydroxide to the oxide, J. Mater. Chem., 5(2):323-9 (1995).

Ansel et al., Pharmaceutical Dosage Forms and Drug Delivery Systems, Chapters 1-8 (pp. 1-243) Lippincott, Williams & Wilkins (1999).

Bejoy, Hydrotalcite: The Clay that Cures, Springer; Resonance, vol. 6 No. 2, pp. 57-61 (2001).

Evonik Industries AG, product information for Eudragit® E100, Eudragit® E POA and Eudragit® E 12,5; pp. 1-6 (Oct. 2011).

De Roy et al., Layered double hydroxides: synthesis and post-synthesis modification, Chapter I, pp. 33-34 In: Rives (ed.), Layered Double Hydroxides: Present and Future, Nova Science Publishers, Inc. (2001).

He et al., Preparation of layered double hydroxides, Struct. Bond., 119:89-119 (2006).

Llewellyn et al., The binding of bile acids by hydrocalcite and other antacid preparations, Pharmaceutica Acta Helvetiae, 52(1/2):1-5 (1977).

Logham-Adham, Safety of new phosphate binders for chronic renal failure, Drug Safety, 26(15):1093-1115 (2003).

Reichle, Synthesis of anionic clay minerals (mixed metal hydroxides, hydrotalcite), Solid State Ionics, 22(1):135-41 (1986).

Adams et al., Formulation of a sterile surgical lubricant, J. Pharm. Pharmacol., 24 Suppl:178P (1972).

Dewberry et al., "Lanthanum carbonate: A novel non-calcium containing phosphate binder", *J Am Soc Nephrol*, 8:A2610 (1997).

Entry for "obtainable", Collins English Dictionary, retrieved from the Internet at <http://www.collinsdictionary.com> on May 15, 2013.

Fernandez et al., The effect of iron on the crystalline phases formed upon thermal decomposition of Mg—Al—Fe hydrotalcites, RCS Publishing: Journal of Materials Chemistry, 8(11):2507-14 (1998).

Forano, Environmental remediationinvolving layered double hydroxides, pp. 426-458, vol. 1, Elsevier Interface Science and Technology (2004).

Goh et al., Application of layered double hydroxides for removal of oxyanions: a review, Water Res., 42:1343-68 (2008).

Hansen et al., Reduction of nitrate to ammonium by sulphate green rust: activation energy and reaction mechanism, Clay Minerals, 33:87-101 (1998).

He et al., Hydrothermal Methods, p. 108 In: Duan et al. (eds.), Layered Double Hydroxides, Springer-Verlag Berlin Heidelberg (2006).

Merriam-Webster's Collegiate Dictionary—11th edition, entry for "prophylaxis" on p. 996 (2004).

Mesh to Micron Conversion chart, retrieved from the Internet at <http:///www.shomegold.org/news/Mesh.htm>, accessed Sep. 27, 2012.

Rankin et al., The development and in-vitro evaluation of novel mixed metal hydroxy-carbonate compounds as phosphate binders, J. Pharm. Pharmacol., 53:361-9 (2001).

Toth et al., Nano-scaled inorganic/biopolymer composites: molecular modeling vistas, AIChE Annual Meeting (2005).

Toth et al., Structure and energetics of biocompatible polymer nanocomposite systems: a molecular dynamics study, Biomacromolecules, 7:1714-9 (2006).

Tsuji et al., Hydrotalcites with an extended $Al^{3+}$-substitution: synthesis, simultaneous TG-DTA-MS study, and their $CO_2$ adsorption behaviors, J. Mater. Res., 8(5):1137-42 (1993).

Cargill et al., Chemical reactivity of aluminium-based pharmaceutical compounds used as phosphate-binders, J. Pharm. Pharmacol., 41:11-16 (1989).

\* cited by examiner

MIXED METAL COMPOUNDS FOR TREATMENT OF HYPERPHOSPHATAEMIA

FIELD OF THE INVENTION

The present invention relates to mixed metal compounds having pharmaceutical activity, especially as phosphate binders. It also extends to methods of manufacture of those compounds, as well as to pharmaceutical compositions containing such compounds. It further relates to their pharmaceutical use.

BACKGROUND OF THE INVENTION

Historically phosphate binders included aluminium salts. However, use of aluminium salts was found to result in toxic complications due to aluminium accumulation, e.g. reduction in haemoglobin production, impairment in natural repair and production of bone and possible impairment of neurological/cognitive function. Other aluminium compounds such as microcrystalline aluminium oxide hydroxide (boehmite) and certain hydrotalcites were proposed for this use, such as disclosed in Ookubo et al, Journal Pharmaceutical Sciences (November 1992), 81 (11), 1139-1140. However these suffer from the same drawbacks.

Calcium carbonate or calcium acetate are now typically used as phosphate binders. However these suffer from the drawback that they tend to promote hypercalcemia through the absorption of high amounts of ingested calcium and are linked to accelerated cardiovascular calcification which can cause serious side effects. Consequently, frequent monitoring of serum calcium levels is required during therapy with calcium-based phosphate binders. The National Kidney Foundation Kidney Disease Quality Outcomes Initiative suggests limiting the use of calcium based salts (Clinical Practice Guidelines for Bone Metabolism and Disease in Chronic Kidney Disease, Guide 5, pg 1 pt 5.5). Recent efforts, therefore, have focused on the development of phosphate binders free of calcium. More recently, lanthanum carbonate and sevelamer HCl have been used as calcium-free phosphate binders. Sevelamer hydrochloride is a water-absorbing, non-absorbed hydrogel-cross-linked polyallylamine hydrochloride but because of its structure also binds certain fat-soluble vitamins and bile acids and is therefore reported in V. Autissier et al, Journal of Pharmaceutical Sciences, Vol 96, No 10, October 2007 to require large doses to be effective because it has a higher propensity for the bound phosphate to be displaced by these competing anions. A high pill burden and/or large tablets are often associated with poor patient compliance and this type of product are also considered relatively expensive to their calcium counter parts. Sevelamer has also been associated with gastro intestinal (GI) adverse effects A. J. Hutchison et al, Drugs 2003; 63 (6), 577-596.

Lanthanum carbonate is a new phosphate binder which has been shown to be as effective as calcium carbonate with lower incidence of hypercalcaemia. Long-term administration of lanthanum, a rare earth element, continues to raise safety concerns with regards to the potential accumulation of a rare earth metal in body tissue which can be enhanced in renal failure—Tilman B Druke, Seminars in Dialysis, Volume 20, Issue 4 page 329-332 July/August 2007.

Many known inorganic preparations for treatment of hyperphosphataemia are efficient phosphate binders only over a limited pH range. Moreover, particularly alkaline binders could buffer the stomach pH up to a high level at which they would not have a phosphate binding capacity.

To overcome the drawbacks associated with aluminium and also problems of efficacy over a limited pH range, WO-A-99/15189 discloses use of mixed metal compounds which are free from aluminium and which have a phosphate binding capacity of at least 30% by weight of the total weight of phosphate present, over a pH range of from 2-8.

Typically, such mixed metal compounds may contain iron (III) and at least one of magnesium, calcium, lanthanum and cerium. Preferably they also contain at least one of hydroxyl and carbonate anions and optionally additionally, at least one of sulphate, nitrate, chloride and oxide. However, mixed metal compounds of WO-A-99/15189 may release some of their magnesium content in soluble form raising serum magnesium levels (Hypermagnesia).

PCT/GB2006/000452 discloses that the release of the divalent metal, e.g. magnesium, associated with the pharmaceutical use of compounds of WO-A-99/15189 can be significantly reduced by heat treatment of a suitable mixed metal compound, for example a layered double hydroxide or a compound having a hydrotalcite structure. However, the divalent metal although in a more acid resistant form than the untreated hydrotalcite structure still comprises sufficient quantities of the divalent metal form for these to be potentially released under extreme acid conditions such as those typically encountered in an empty stomach.

Seida et al (Water research 36 2002 1306-1312) discloses that phosphate binding by layered double hydroxides containing iron increases at a pH value maintained at pH 6.86 due to a combination of anion-exchange as well as precipitation or coagulation of the released divalent metal ion binding with phosphate. This compound was separated from the phosphate solution in order to determine the residual phosphate concentration in the solution. The isolated compound was not dried or milled and not intended for use as a new phosphate binder. Moreover the compound was already partially bound to phosphate thereby reducing remaining sites available for further phosphate binding. In addition, the teaching of Seida et al suggests that the presence of magnesium in the mixed metal compounds plays an important part in producing sufficient precipitation and increasing phosphate binding.

J. Das et al teaches that layered double hydroxides increasingly dissolve at pH values below 6 with a further decrease in phosphate binding. Ookubo et al (Langmuir 1993, 9, 1418-1422) teaches that layered double hydroxides (referred to as hydrotalcites) are soluble in strong acidic media and should only be used as drugs when the hydrotalcite is protected by an enteric acid resistant coating. However, enteric coated drugs would be acid resistant as well as being resistant to phosphate binding. Furthermore, Ookubo and Shin et al, Wat. Sci. Tech. 1996, Vol 34, No 1-2, page 161-168 teaches that the carbonate of hydrotalcite-type materials is not readily replaced by other anions and that chlorine comprising hydrotalcites should be used for binding phosphate.

J. Das et al, Applied Clay Science 32 2006 252-260 discloses magnesium aluminium mixed metal layered hydroxide compounds with a divalent:trivalent metal range of 2:1 to 4:1 wherein the phosphate binding decreases with increasing divalent:trivalent metal ratio. It is believed that the higher amount of the trivalent metal increases phosphate binding because it creates a higher net positive charge on the hydroxide layer compared to samples with less of the trivalent metal. However, the examples described in Das et al teach divalent:trivalent metal molar ratios not lower than 2:1. Moreover, Rives et al, Layered Double Hydroxides Present and Future, teaches that the preferred lower limit is 2:1 and not exceeding a ratio less than 1:1. Mg-depleted mixed metal compounds of divalent:trivalent ratios less than 2:1 were prepared in our laboratory either via modification of coprecipitation or precipitation methods described in WO-A-99/15189 by controlling the pH at a lower pH (i.e. pH value of 5) during the reaction-stage, which is in contrast to the teaching of WO-A-99/15189 describing an optimum pH range of 10-10.5. Alternatively, the mixed metal compounds of WO-A-99/15189 were treated after the precipitation reaction-stage (i.e. post-synthesis), with a depleting agent. Treatment of mixed metal compounds of WO-A-99/15189 containing carbonate anion with hydrochloric acid are preferred because they were found to result either in compounds with good phosphate binding but with lower release of the divalent cation and/or showed a decreased presence of a mixture of single metal compounds of $M^{II}(OH)_2$, $M^{II}(OH)_3$, un-reacted reagents or other non hydrotalcite crystalline phases. Furthermore, mixtures prepared by simply admixing two different single metal salts at equivalent ratio to the Mg-depleted compound were also found to have lower phosphate binding or more release of the divalent cation (Table 2).

Phosphate binders based on single metal types such iron-oxide-hydroxide FeOOH are disclosed in US617444 and EP1932808 or LaCarbonate disclosed in US2008/0187602 but require the presence of carbohydrate stabilisers to prevent time ageing and transformation into iron-oxides or La hydroxycarbonates during manufacture and typically have a lower phosphate binding capacity.

Thus there is an urgent and widespread need for a more effective phosphate binder which does not release trivalent or divalent ions into the blood stream, does not require enteric coating and which is effective over a wide pH range of from 2-8.

In one aspect the present invention provides a pharmaceutical composition comprising
(a) a mixed metal compound according to formula (I)

$$M^{II}_{1-a}M^{III}_a \quad (I)$$

wherein $M^{II}$ is at least one bivalent metal;
$M^{III}$ is at least one trivalent metal; and
$1>a>0.4$;
the compound contains at least one n-valent anion $A^{n-}$ such that the compound is charge neutral; and
(b) a pharmaceutically acceptable carrier, diluent, excipient or adjuvant.

It will be understood that $$a = \frac{\text{number of moles of } M^{III}}{(\text{number of moles of } M^{II} + \text{number of moles of } M^{III})};$$

In a further aspect the present invention provides a mixed metal compound for use as a medicament wherein the mixed metal compound is of formula (I)

$$M^{II}_{1-a}M^{III}_a \quad (I)$$

wherein $M^{II}$ is at least one bivalent metal;
$M^{III}$ is at least one trivalent metal; and
$1>a>0.4$;
the compound contains at least one n-valent anion $A^{n-}$ such that the compound is charge neutral.

In a further aspect the present invention provides use of a mixed metal compound in the manufacture of a medicament for binding phosphate, wherein the mixed metal compound is of formula (I)

$$M^{II}_{1-a}M^{III}_a \quad (I)$$

wherein $M^{II}$ is at least one bivalent metal;
$M^{III}$ is at least one trivalent metal; and
$1>a>0.4$;
the compound contains at least one n-valent anion $A^{n-}$ such that the compound is charge neutral.

In a further aspect the present invention provides use of a mixed metal compound in the manufacture of a medicament for the prophylaxis or treatment of any one of hyperphosphataemia, renal insufficiency, hypoparathyroidism, pseudo-hypoparathyroidism, acute untreated acromegaly, chronic kidney disease (CKD), clinically significant change in bone mineralization (osteomalecia, adynamic bone disease, osteitis fibrosa), soft tissue calcification, cardiovascular disease associated with high phosphates, secondary hyperparathyroidism, over medication of phosphate salts and other conditions requiring control of phosphate absorption, wherein the mixed metal compound is of formula (I)

$$M^{II}_{1-a}M^{III}_a \quad (I)$$

wherein $M^{II}$ is at least one bivalent metal;
$M^{III}$ is at least one trivalent metal; and
$1>a>0.4$;
the compound contains at least one n-valent anion $A^{n-}$ such that the compound is charge neutral.

In a further aspect the present invention provides a mixed metal compound of formula (IV)

$$[M^{II}_{1-a}M^{III}_a O_b(OH)_d](A^{n-})_c \cdot zH_2O \quad (IV)$$

wherein is at least one bivalent metal selected from Mg (II), Zn (II), Fe (II), Cu (II), Ca (II), La (II), Ce (II) and Ni (II);
$M^{III}$ is at least one trivalent metal selected from Mn(III), Fe(III), La(III) and Ce(III); and
$A^{n-}$ is at least one n-valent anion and wherein at least one anion is carbonate;
$1>a>0.4$;
$0 \leq b \leq 2$
the value of c for each anion is determined by the need for charge neutrality as expressed by the formula $2+a-2b-d-cn=0$; and
$0 \leq d \leq 2$.
$0 < z \leq 5$.

In a further aspect the present invention provides a mixed metal compound obtained by or obtainable by treatment with an acid, a chelating agent or a mixture thereof of a compound $$[M^{II}_{1-a}M^{III}_a O_b(OH)_d](A^{n-})_c \cdot zH_2O \quad (IV)$$

wherein $M^{II}$ is at least one bivalent metal selected from Mg (II), Zn (II), Fe (II), Cu (II), Ca (II), La (II), Ce (II) and Ni(II);
$M^{III}$ is at least one trivalent metal selected from Mn(III), Fe(III), La(III) and Ce(III); and
$A^{n-}$ is at least one n-valent anion and wherein at least one anion is carbonate;
$0 < a \leq 0.4$;
$0 \leq b \leq 2$.
the value of c for each anion is determined by the need for charge neutrality as expressed by the formula $2+a-2b-d-cn=0$; and
$0 \leq d \leq 2$.
$0 < z \leq 5$.

In a further aspect the present invention provides a process for the production of a magnesium-depleted mixed metal compound of formula (IV)

$$[M^{II}_{1-a}M^{III}_a O_b(OH)_d](A^{n-})_c \cdot zH_2O \quad (IV)$$

wherein $1>a>0.4$;
the process comprising the steps of:
a) contacting a compound of formula (IV)

$$[M^{II}_{1-a}M^{III}_a O_b(OH)_d](A^{n-})_c \cdot zH_2O \quad (IV)$$

wherein $0<a \leq 0.4$;
with an acid, a chelating agent or a mixture thereof; and
b) optionally subjecting the resulting compound to heat treatment.

wherein is at least one bivalent metal selected from Mg (II), Zn (II), Fe (II), Cu (II), Ca (II), La (II), Ce (II) and Ni(II); $M^{III}$ is at least one trivalent metal selected from Mn(III), Fe(III), La(III) and Ce(III); and
$A^{n-}$ is at least one n-valent anion and wherein at least one anion is carbonate;
b 2.
the value of c for each anion is determined by the need for charge neutrality as expressed by the formula $2+a-2b-d-cn=0$; and
$0 \leq d \leq 2$.
$0 < z \leq 5$.

In a further aspect the present invention provides a pharmaceutical composition comprising
(a) a compound of the present invention or obtained/obtainable in accordance with the present invention, and
(b) a pharmaceutically acceptable carrier, diluent, excipient or adjuvant.

In a further aspect the present invention provides a compound of the present invention or obtained/obtainable in accordance with the present invention for use as a medicament.

In a further aspect the present invention provides use of a compound of the present invention or obtained/obtainable in accordance with the present invention in the manufacture of a medicament for binding phosphate.

In a further aspect the present invention provides use of a compound of the present invention or obtained/obtainable in accordance with the present invention in the manufacture of a medicament for the prophylaxis or treatment of any one of hyperphosphataemia, metabolic bone disease, metabolic syndrome, renal insufficiency, hypoparathyroidism, pseudohypoparathyroidism, acute untreated acromegaly, chronic kidney disease (CKD), clinically significant change in bone mineralisation (osteomalecia, adynamic bone disease, osteitis fibrosa), soft tissue calcification, cardiovascular disease associated with high phosphates, secondary hyperparathyroidism, over medication of phosphate salts and other conditions requiring control of phosphate absorption.

Furthermore the present invention provides a process for preparation of depleted compounds comprising oxide-hydroxide of metal having a M-O bond distance of approximately $2 \oplus$ (angstrom) as determined by Extended X-Ray Absorption Fine Structure (EXAF) studies. More specifically, for depleted compound derived from a Mg Fe mixed metal compound (example A), the distance between the centre absorbing iron atom and its nearest oxygen atom neighbour is $1.994 \oplus$ ($1^{st}$ shell distance). The distance between the centre absorbing iron atom and its nearest iron neighbour (M-O-M distance) is $3.045 \oplus$ ($2^{nd}$ shell distance). A preferred range M-O bond distance is between $1.5-2.5 \oplus$ and a preferred range of M-O-M distance is between $2-4 \oplus$.

We have found surprisingly that under controlled conditions it is possible to remove the more soluble metal from the mixed metal compounds such as layered hydroxide structure or a heat-treated mixed metal compound whilst maintaining mixed metal compounds with divalent:trivalent molar ratios less than 1 with a typical hydrotalcite XRD signature, thereby creating metal-depleted mixed metal compounds with improved or maintained phosphate binding and a lower release of divalent or trivalent metal ions (such as magnesium) during the phosphate binding reaction. In addition or alternatively, the metal-depleted mixed metal compound may be heat-treated to increase phosphate-binding and reduce metal (e.g. magnesium) release further. The metal-depleted mixed metal compound has superior phosphate binding characteristics to the mixed metal compounds of WO-A-99/15189 and PCT/GB2006/000452. The metal-depleted mixed metal compound may be magnesium depleted. The magnesium-depleted mixed metal compound comprises a lower content of the more soluble divalent magnesium ion and more of the less soluble trivalent iron resulting in ratios of divalent Mg:trivalent Fe range significantly less than those previously reported for solid mixed metal compounds used for phosphate binding.

We have found that by using the carbonate instead of sulphate anion in the starting material, acidification of the mixed metal compound results in a cleaner compound i.e. with lower amounts of sulphates salts remaining in the depleted product; this is because of the acidification of the carbonate anion only leads to formation of water and carbon dioxide.

By mixed metal compound, it is meant that the atomic structure of the compound includes the cations of at least two different metals distributed uniformly throughout its structure. The term mixed metal compound does not include mixtures of crystals of two salts, where each crystal type only includes one metal cation. Mixed metal compounds are typically the result of coprecipitation from solution of different single metal compounds in contrast to a simple solid physical mixture of 2 different single metal salts. Mixed metal compounds as used herein include compounds of the same metal type but with the metal in two different valence states e.g. Fe(II) and Fe(III) as well as compounds containing more than 2 different metal types in one compound.

The mixed metal compound may also comprise amorphous (non-crystalline) material. By the term amorphous is meant either crystalline phases which have crystallite sizes below the detection limits of x-ray diffraction techniques, or crystalline phases which have some degree of ordering, but which do not exhibit a crystalline diffraction pattern and/or true amorphous materials which exhibit short range order, but no long-range order.

The substances of the invention may contain at least one compound of formula (I) or (IV). The process of preparing (such as) depleting the compound may also result in other materials being present in addition to compounds of formula (I) or (IV), for example single (as opposed to mixed) metal compounds may also be formed during the process.

The process for preparing compounds of formula (I) or (IV) may result in changes in the structure of the compound which is the starting material. Therefore the formula (I) or (IV) describe only the elemental composition of compounds of formula (I) or (IV) and do not provide a definition of structure The compound of the present invention or for use in the present invention is preferably formed with no aging or hydrothermal treatment to avoid the crystals of the compound growing in size and to maintain a high surface area over which phosphate binding can take place. The compound of formula I is also preferably maintained in a fine particle size form during the post-synthesis route to maintain good phosphate binding. Preferably 90% of the compound of formula I based on volume (d90) has a particle size of less than 200 micron, more preferably 90% of the compound of formula I based on volume (d90) has a particle size of less than 100 micron, most preferably 90% of the compound of formula I based on volume (d90) has a particle size of less than 50 micron.

The compound of the present invention may also be prepared in the form of granulates. When comprised in the granulate form it is preferred that 90% of the compound of formula I based on volume (d90) has a particle size of less than 1000 micron, more preferably 90% of the compound of formula I based on volume (d90) has a particle size of less than 750 micron, most preferably 90% of the compound of formula I based on volume (d90) has a particle size of less than 500 micron even more preferred 90% of the compound of formula I based on volume (d90) has a particle size of less than 250 micron.

As used herein, the term "Layered Double Hydroxide" (LDH) is used to designate synthetic or natural lamellar hydroxides with two kinds of metallic cations in the main layers and interlayer domains containing anionic species. This wide family of compounds is sometimes also referred to as anionic clays, by comparison with the more usual cationic clays whose interlamellar domains contain cationic species. LDHs have also been reported as hydrotalcite-like compounds by reference to one of the polytypes of the corresponding [Mg—Al] based mineral. (See "Layered Double Hydroxides: Present and Future", ed, V Rives, 2001 pub. Nova Science).

For ease of reference, these and further aspects of the present invention are now discussed under appropriate section headings. However, the teachings under each section are not necessarily limited to each particular section.

PREFERRED ASPECTS

As discussed herein the mixed metal compound for use in the invention (such as in the composition of the present invention) may be of formula (I)

$$M^{II}_{1-a}M^{III}_{a} \qquad (I)$$

wherein $M^{II}$ is at least one bivalent metal;
$M^{III}$ is at least one trivalent metal; and
$1>a>0.4$;
the compound contains at least one n-valent anion $A^{n-}$ such that the compound is charge neutral.

Preferably the mixed metal compound is of formula (IV)

$$[M^{II}_{1-a}M^{III}_{a}O_b(OH)_d](A^{n-})_c \cdot zH_2O \qquad (IV)$$

wherein $M^{II}$ is at least one bivalent metal;
$M^{III}$ is at least one trivalent metal; and
$1>a>0.4$;
$0 \le b \le 2$;
the value of c for each anion is determined by the need for charge neutrality as expressed by the formula $2+a-2b-d-cn=0$; and
$0 \le d \le 2$
$0 \le z \le 5$.

$M^{II}/M^{III}$

The at least one bivalent metal ($M^{II}$) may be selected from any suitable metal. $M^{II}$ is preferably selected from Mg (II), Zn (II), Fe (II), Cu (II), Ca (II), La (II), Ce (II) and Ni(II). $M^{II}$ is further preferably selected from Mg (II), Zn(II), Fe (II), Cu (II) and Ni(II). Of these, Mg is especially preferred.

The at least one trivalent metal ($M^{III}$) may be selected from any suitable metal. $M^{III}$ is preferably selected from Al (III), Mn(III), Fe(III), La(III) and Ce(III). $M^{III}$ is preferably selected from Mn(III), Fe(III), La(III) and Ce(III). Of these, Fe(III) is especially preferred, particularly in the case when $M^{II}$ is Mg. $M^{II}$ and $M^{III}$ may be different metals or they may be the same metal but in different valence states. For instance, $M^{II}$ may be Fe(II) and $M^{III}$ Fe(III). However it is highly preferred that $M^{II}$ and $M^{III}$ are different metals. M(III) may also be Al(III) for treatments where aluminium accumulation and toxic complications are not a problem. Preferably, any substance of the invention is substantially or totally free of aluminium.

Fe(III) is especially preferred as results demonstrate that this metal does not dissolve simultaneously with the Mg(II) during the depletion process thereby enabling the formation of a Mg-depleted compound. In contrast, mixed metal compounds prepared from Mg Al were more difficult to deplete because of a more similar dissolution profile of the Mg and Al metal resulting in compounds of more equimolar ratios.

$A^{n-}$

The anions $A^{n-}$ may be selected such that the requirement that compound be charge neutral is satisfied. $A^{n-}$ preferably comprises at least one anion selected from carbonate, hydrogencarbonate, sulphate, nitrate, halide and hydroxide. Of these, carbonate is especially preferred.

It is preferred that the n-valent anion $A^{n-}$ an exchangeable anion thereby facilitating the exchange of the phosphate for the $A^{n-}$ valent anion in the solid mixed metal compound.

In a highly preferred aspect the mixed metal compound for use in the invention (such as in the composition of the present invention) may be a compound of formula (IV)

$$[M^{II}_{1-a}M^{III}_{a}O_b(OH)_d](A^{n-})_c \cdot zH_2O \qquad (IV)$$

wherein $M^{II}$ is at least one bivalent metal selected from Mg (II), Zn (II), Fe (II), Cu (II), Ca (II), La (II), Ce (II) and Ni(II);
$M^{III}$ is at least one trivalent metal selected from Mn(III), Fe(III), La(III) and Ce(III); and
$A^{n-}$ is at least one n-valent anion and wherein at least one anion is carbonate;
$1>a>0.4$;
$0 \le b \le 2$;
the value of c for each anion is determined by the need for charge neutrality as expressed by the formula $2+a-2b-d-cn=0$; and
$0 \le d \le 2$.
$0 < z \le 5$.
d As discussed herein $0 \le d \le 2$.

In one aspect d may be is 0. Thus there is provided a compound of formula (II):

$$M^{II}_{1-a}M^{III}_{a}O_b A^{n-}_{c} \cdot zH_2O \qquad (II)$$

wherein $M^{II}$ is at least one bivalent metal selected from Mg (II), Zn (II), Fe (II), Cu (II), Ca (II), La (II), Ce (II) and Ni(II);
$M^{III}$ is at least one trivalent metal selected from Mn(III), Fe(III), La(III) and Ce(III); and
$A^{n-}$ is at least one n-valent anion and wherein at least one anion is carbonate;
$1>a>0.4$;
$0 \le b \le 2$.
the value of c for each anion is determined by the need for charge neutrality as expressed by the formula $2+a-2b-cn=0$ and $\Sigma cn<0.9a$ and
$0<z \le 5$.

When d is 0, preferably $\Sigma cn<0.9a$.

In a further aspect d is other than zero. Thus $0<d \le 2$ is envisaged.

In one aspect $0<d \le 2$. Preferably d is 1.5 or less, even more preferably d is 1 or less.

The present invention provides for
$0<d \le 1$
$0 \le d \le 1$

In one aspect b may be 0. Thus there is provided a compound of formula (III)

$$M^{II}_{1-a}M^{III}_{a}(OH)_d A^{n-}_{c} \cdot zH_2O \qquad (III)$$

wherein $M^{II}$ is at least one bivalent metal selected from Mg (II), Zn (II), Fe (II), Cu (II), Ca (II), La (II), Ce (II) and Ni(II);

$M^{III}$ is at least one trivalent metal selected from Mn(III), Fe(III), La(III) and Ce(III); and
$A^{n-}$ is at least one n-valent anion and wherein at least one anion is carbonate;
$1 > a > 0.4$;
the value of c for each anion is determined by the need for charge neutrality as expressed by the formula $2+a-d-cn=0$;
$\Sigma cn < 0.9a$ and
$0 \leq d \leq 2$
$0 < z \leq 5$.

In a further aspect b is other than zero. Thus $0 < b \leq 2$ is envisaged.

Preferably b is 1.5 or less, 1.2 or less or preferably 1 or less. The present invention provides for
$0 < b \leq 1.5$
$0 \leq b \leq 1.5$
$0 < b \leq 1.2$
$0 \leq b \leq 1.2$
$0 < b \leq 1$
$0 \leq b \leq 1$ c If b is not 0; preferably c is 0.5 or preferably 0.15 or less. The present invention provides for
$0 < c \leq 0.5$
$0 < c \leq 0.15$
$0 \leq c \leq 0.15$
$0.01 < b \leq 0.15$
$0.01 \leq b \leq 0.15$ z Preferably z is 5 or less, preferably z is 2 or less, 1.8 or less or preferably 1.5 or less. The present invention provides for
$0 < z \leq 5$
$0 < z \leq 2$
$0 \leq z \leq 2$
$0 < z \leq 1.8$
$0 \leq z \leq 1.8$
$0 < z \leq 1.5$
$0 \leq z \leq 1.5$ a As will be understood from the description of the invention provided herein, a may be any value between 1 and 0.4. Thus $1 > a > 0.4$.

Preferred aspects of the invention are provided wherein
$1. > a > 0.4$.
$0.98 > a > 0.5$.
$0.98 > a > 0.6$
$0.98 > a \geq 0.7$.
$0.95 > a \geq 0.7$
$0.90 > a \geq 0.7$
$0.85 > a \geq 0.7$
$0.80 > a \geq 0.7$ The increase of the value of "a" above 0.98 results in more significant reduction in phosphate binding of up to 75%. Without being bound by theory it is believed that the decreased phosphate binding for values of "a" above 0.98 results from the complete removal of the divalent metal (magnesium); furthermore, the yield (the amount of phosphate binder isolated after the depletion-reaction) is reduced significantly because of loss of the iron. This makes the compound structurally unstable and thereby less effective as a phosphate binder. Whereas if the value of "a" is $0.98 > a \geq 0.7$ phosphate binding may be reduced by only approx 10%. If the value of "a" is below 0.7 phosphate binding is either higher or maintained. If the "a" value is above 0.8 the potential for release of the divalent metal (magnesium) is still more than 50% of the total available amount of divalent metal present in un-depleted phosphate binder thereby providing the potential undesirable release of metal. Consequently a preferred range is between $0.80 > a \geq 0.7$ as this provides the best compromise between good phosphate binding and lower amounts of divalent metal available for dissolution. Coincidentally, this also falls within the pH region of 4-6 whereby the largest pH buffering is observed of the undepleted material and where a transformation from the presence of a crystalline (hydrotalcite) to a non-crystalline structure is observed (table 3). Typically the yield of the depletion reaction is not less than 50% if $a \geq 0.7$ (table 5).

In addition, depleted compounds of "a" values above 0.95 are more difficult to consistently manufacture and phosphate binding is reduced and approaches that of a sample of FeOOH ("a" value is 1). As discussed hereinbefore, pure FeOOH compounds are less stable and require the presence of a stabilising agent e.g. carbohydrate.

For values of "a" obtainable from the compounds isolated from a solution maintained at pH values of 8, 9 or higher, phosphate binding occurs mainly only through ion-exchange of the phosphate anion in solution with the anion present in the solid layered double hydroxide or mixed metal compound. The maximum phosphate binding capacity of the layered double hydroxides structure or the mixed metal compounds with values of "a" below 0.4 are then limited by the amount of the exchangeable anion and its associated charge within the starting material, in addition, the available size of the space between the layers of the mixed metal compound is also restricting the exchange of phosphate at "a" values below 0.4. Values of "a" above 0.4 are known to those skilled in the art to lead to less stable layered double hydroxide structures and these compositions have therefore previously not been considered as effective binders of anions such as phosphate. Surprisingly we have found that despite the gradual loss of the typical layered double hydroxide or hydrotalcite structure, phosphate binding actually increases or is typically maintained at values of "a" above that of 0.4 and only decreases significantly when "a" is above 0.98. It is believed that the higher amount of the trivalent metal maintains good phosphate binding because of a higher net positive charge on the metal hydroxide layers compared to samples with less of the trivalent metal but without the restrictions in phosphate binding observed for those compounds of "a" values below 0.4. Moreover we found that single metal trivalent metal hydroxide such as ferric hydroxides or ferric citrate compounds are less effective phosphate binders showing that the presence of some divalent metal is preferred but not at levels resulting in ratios of mixed metal compounds of those of "a" values below 0.4. In addition, simple mixtures prepared from mixtures of magnesium and iron salts are not as effective (table 2).

In effect because of exposure of the metal based phosphate binders to a depleting agent, prior to use as a medicament, release of solubilised metal is significantly reduced upon subsequent further contact with gastric acid in the stomach, whilst surprisingly maintaining good phosphate binding activity in the gut.

Process

As discussed herein the present invention provides a process for the production of a magnesium-depleted mixed metal compound of formula (IV)

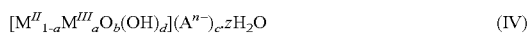   (IV)

wherein $1 > a \geq 0.4$;
the process comprising the steps of:
a) contacting a compound of formula (IV)

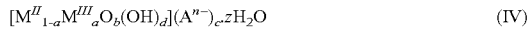   (IV)

wherein $0 < a \leq 0.4$;
with an acid, a chelating agent or a mixture thereof; and
b) optionally subjecting the resulting compound to heat treatment.

wherein $M^{II}$ is at least one bivalent metal selected from Mg (II), Zn (II), Fe (II), Cu (II), Ca (II), La (II), Ce (II) and Ni(II);
$M^{III}$ is at least one trivalent metal selected from Mn(III), Fe(III), La(III) and Ce(III); and
$A^{n-}$ is at least one n-valent anion and wherein at least one anion is carbonate;
$0 \leq b \leq 2$.
the value of c for each anion is determined by the need for charge neutrality as expressed by the formula $2+a-2b-d-cn=0$; and
$0 \leq d \leq 2$
$0 < z \leq 5$;
and a mixed metal compound obtained by or obtainable by said process.

In one aspect of the present invention the compound obtained by the treatment of a compound of formula (IV) wherein $0 < a \leq 0.4$ is further subjected to heat treatment. The term "heat treatment" can mean calcination.

Suitably, the structures are depleted in metal using a depleting agent selected from HCl, $H_2SO_4$, citric acid, EDTA, $HNO_3$, acetic acid and aluminium sulphate $[Al_2(SO_4)_3]$ and combinations hereof. Preferably the acid or chelating agent is hydrochloric acid.

The process of depletion may also be used for other existing phosphate binders. Preferably this would be for metal base binders but may also be used for non-metal based phosphate binders such as sevelamer type polymers.

The concentration of the depleting agent may range from about 0.01M to about 5M. Suitably, the structures are depleted (such as in magnesium) using depleting agent of concentration 0.01 M to 5 M, preferably a concentration from 0.1 to 2 M, more preferably from 0.5 to 1.5 M.

Preferably the process provides a reduction of the amount of metal $M^{II}O$ by at least 10% by weight compared to that of the untreated compound of formula (IV).

The treatment with hydrochloric acid (HCl) is suitably carried out with HCl of concentration 0.01 M to 5 M, preferably a concentration from 0.1 to 2 M, more preferably from 0.5 to 1.5 M.

The compound of formula (IV) wherein $0 < a \leq 0.4$ may be treated for a period of 5 minutes or longer, more preferably 15 minutes or longer, more preferably 1 hour or longer.

The compound of formula (IV) wherein $0 < a \leq 0.4$ may be preferably treated for 1 hour or less, more preferably 30 minutes or less, even more preferably 15 minutes or less.

The optimum in treatment time may vary depending on the conditions of the treatment e.g. amount of starting material, acid concentration, type of acid, treatment pH etc. The optimum treatment time will be shorter when using stronger acids whereas optimum treatment time will increase with weaker acid strengths.

Preferably, the acid strength is not too weak (less than 0.1 M), as this would increase production time as well as increasing the volume of acid required.

The treatment as described above results in the reduction of the divalent metal ion from the compound according to formula (IV). The treatment is believed to lead to the formation of a compound according to the invention. This results in the value of a for a compound according to formula (IV) being equal to or larger than the value of a for the corresponding untreated compound according to formula (IV).

The depletion treatment is preferably not excessive in terms of acid and/or chelating agent concentration and/or time of exposure, by which it is meant that the treatment should not exceed treatment for more than 2 hours, otherwise a phosphate binding performance which is less than optimal may be found.

Treatment with acid below pH=3 (i.e. contacting the compound for a sufficient time with acid until an equilibrium pH 3 is reached and then maintaining at the equilibrium value for sufficient time—typically a 30 minutes time period was used for the total of the initial addition and for maintaining the pH constant) results in the increase of the value of a to more than 0.98 and significant reduction in phosphate binding. Hence it is preferred that a is less than 0.99, more preferably less than 0.95, even more preferably less than 0.9, most preferably less than 0.85. Excessive treatment with acid may lead to complete dissolution of the compound with significant reduction in phosphate binding performance or yield of preparation, hence it is preferred that the substances of the invention are not completely dissolved.

Treatment with acid at or below pH 5 results in complete loss of the hydrotalcite XRD signal. Without being bound by theory, it is believed that the divalent metal-depleted compounds obtained at pH of 5 or less are the result of the transition from the crystalline hydrotalcite into a non-crystalline phase. The non-crystalline phase is structurally stable but when obtained at pH values of pH 3 or below will also start releasing the trivalent metal ions. Consequently, there is an optimum pH range to which the material is depleted. Depleted compounds obtained at pH 5 typically have a value for a of not more than 0.85 and so it is preferred if the compound of formula (I) has a value for a of 0.85 or less, preferably 0.8 or less, but not less than 0.4, preferably not less than 0.5, most preferably not less than 0.6, most preferably not less than 0.7. A value of a of not less than 0.7 is preferred because the depleted compound of an a value of 0.7 has approximately a 50% reduction of the release of the divalent metal into solution during the phosphate binding. Assuming equivalent phosphate binding capacity, an equivalent average daily dose of magnesium-depleted Mg Fe mixed metal compound (i.e. 3 to 4.5 g of example A) containing 50% less magnesium would be expected to increase serum magnesium by between 0.12 and 0.18 mmol/l whereas an increase of 0.24 and 0.36 mmol/l would be expected for use of the equivalent compound with no depletion when taken by kidney patients. In contrast, subjects with normal functioning kidneys would not see an increase in serum magnesium when taking either the depleted compound or the un-depleted compound from an average baseline of 0.95 mmol/l. A controlled use of a small (i.e. leading to an increase serum magnesium of less than 0.12 mmol/l) but not excessive (i.e. leading to an increase of serum magnesium of more than 0.24 mmol/l) amount of magnesium supplementation may be of benefit to healthy subjects or kidney patients.

Preferably, treatment of the compound of formula (IV) results in a substance with at least a 5% higher phosphate binding capacity when measured according to the standard phosphate binding method (Test Method 1a) or not more than 25% reduction in phosphate binding capacity when measured according to the representative test method (Test Method 1b or method 1c or 1d) relative to that of the compound of formula (IV) from which the substance is obtained or obtainable by treatment with acid or chelating agent.

A suitable method for monitoring the degree of acid addition is by continuous measurement of the pH with a pH meter (Jenway 3520) using a combined glass electrode (VWR 6621759). The pH meter was calibrated with buffers of pH 4, 7 and 10 before any measurement. The pH of the solution was adjusted using minimum volume of the acid and/or chelating agent solution at room temperatures 20+/−5° Celsius. The total volume added for pH adjustment never exceeded 60% of the total volume.

A suitable method for monitoring the divalent metal depletion of the compound is by measurement of the metal oxide content, i.e. where the compound is magnesium depleted by measuring the MgO content. This is measured by XRF (PW2400 Wavelength Dispersive XRF Spectrometer).

Another suitable method for monitoring the divalent metal depletion of the compound is by measurement of the magnesium released from the compound during the phosphate binding.

Suitably, the magnesium-depleted mixed metal compound after treatment has less than 28%, preferably less than 25%, more preferably less than 20% but does not have less than 0.5% by weight MgO content.

Preparation

Phosphate is also believed to bind to the depleted compound through a direct ionic interaction between one or two negatively charged oxygen ions on the phosphate with the M(III) metal centre in the solid through displacement of hydroxide.

It was discovered that the biggest increase in phosphate binding and/or reduction in magnesium release was found for those compounds isolated from solution where the pH was within the pH buffering region of the starting material from which the M(II) depleted material was derived. For example, the mixed metal compound A (table 3), has pH buffering properties between pH 3 and 8 and most significantly between 5 and 7. The Mg-depleted compounds isolated from compound "A" all showed higher phosphate binding (phosphate binding test method 1A) when isolated at pH between 3 and 8 than for those isolated at pH values of 3, 8 or 9. Depleted compounds isolated at very low pH (pH 3 or less) resulted in lower phosphate binding, lower yield and also more significant dissolution of the trivalent cation whereas depleted compounds isolated at high pH values 8 or 9 were not sufficiently depleted to improve phosphate binding above that of the starting material or showed more release of the divalent metal.

The increase in phosphate removal by the M(II) depleted compound correlates with the increase in pH buffering capacity when measured with the standard test method 1a of the mixed metal compound from which the M(II) depleted completed compound was derived. Consequently, the presence of hydroxide (OH) groups in the M(II)-depleted compound is preferred for binding phosphate such as of formula: $M^{II}_{1-a}M^{III}_{a}(OH)_d$, $[M^{II}_{1-a}M^{III}_{a}(OH)_d](A^{n-})_c$ or formula (I) (III) or (IV) wherein $1>a>0.4$ and $0<d\leq2$.

Since phosphate binding will also take place at the surface of the M(II) depleted solid, the amount of surface area is one important attribute in determining how much phosphate the M(II) depleted compound can bind. Preferably, a surface area of more than 10 $m^2/g$, preferably more than 50 $m^2/g$ even more preferably more than 100 $m^2/g$, most preferably more than 250 $m^2/g$.

Compounds of the invention or for use in the invention are preferably made by acid treatment with hydrochloric acid of a suitable starting material as hereinbefore described. Optionally other chemicals may be employed to prepare the substance of invention such as using other acids and chelating agents. Optionally other preparation-routes may be used such as treatment of slurries, moist filtration cakes containing the compound, wet-cakes, milled, un-milled forms of the dried compound or even by controlling the pH during the reaction-stage. Preferably, at a pH less than 10 but not less than pH=3; between this range pH 5 is preferred. Optionally, the recipe for the co-precipitation route may be changed by using a smaller amount of the divalent salt (i.e. $MgSO_4$). Optionally other conditions may be used for example high or low temperature or pressure conditions.

The substances of the invention prepared by treatment of a suitable starting material as hereinbefore described may be prepared by providing a first solution of a water soluble compound of metal $M^{II}$ and a water soluble compound of metal $M^{III}$, the anions being chosen so as not to result in precipitation from the first solution. A second solution is also provided, of a water soluble hydroxide (e.g. NaOH) and a water soluble salt of anion $A^{n-}$ (the cation being chosen so as not to precipitate with the hydroxide or the anion with the metal from the hydroxide). The two solutions are then admixed and the mixed metal compound starting material is formed by co-precipitation. It comprises solid crystalline material, usually also with the presence of some solid amorphous material. Preferably, at least some of the material so formed is of a layered double hydroxide and/or of a hydrotalcite structure, usually also with some amorphous and/or poorly crystalline material, preferably after co-precipitation, the material is then filtered or centrifuged, washed then dried by heating.

The starting material may be prepared by heat treatment (calcination) of the starting material. Alternatively, the depleted material may be heat-treated (calcination) preferably at temperatures equal to or less than 500° C. to improve phosphate binding. Calcination temperatures of equal to or less than 500° C. are preferred to avoid formation of spinel type compounds and optimise phosphate binding.

It is preferred that the material is washed in order to remove the water-soluble salts that are the by product of the treatment. If significant amounts of these soluble salts are left admixed with the isolated solid, then the subsequent solid may potentially have an adverse effect on its phosphate binding behaviour. The material is preferably washed such that the remaining level of water soluble salts (having a solubility in water of 1 g/liter or more) is less than 15%, preferably less than 10%, more preferably less than 5% by weight of the solid mixed metal compound after drying as described below. Especially because of the depletion process (for example with acid treatment with HCl) water-soluble salts of divalent metals (i.e. $MgCl_2$) are formed which are the by product of the depletion treatment. We have found that a larger number of repeat wash cycles is required to remove the water-soluble salts.

After isolation of the depleted compound (with any means of isolation such as filtration, centrifugation or decantation) and washing, the drying is preferably carried out at low temperature (such as to provide a product or oven temperature of up to 120° C.), for example by oven drying, spray drying or fluid bed drying.

Optionally, the dry material may be classified prior to acid-treatment, to remove oversize particles by milling and/or sieving and/or any other suitable technique, for example to restrict the material to be treated to particles which are substantially no greater than 100 μm in diameter. Preferably, as measured by sieving, less than 10% by weight of particles are greater than 106 μm in diameter, more preferably less than 5%. Most preferably, no particles are greater than 106 μm in diameter as measured by sieving.

The dry material is typically directly subjected to the necessary treatment, preferably with HCl of concentration 0.01 M to 5 M, preferably a concentration from 0.1 to 2 M, more preferably from 0.5 to 1.5 M for a period of 5 minutes or longer, more preferably 15 minutes or longer, more preferably 1 hour or longer. The compound is preferably treated for 1 hour or less, more preferably 30 minutes or less, even more preferably 15 minutes or less.

Optionally, the moist filter cake or slurry material may be directly subjected to the treatment.

A preferred process in accordance with the present invention is recited below:

Taking (20 g of) compound comprising a compound of formula (II)

$$M^{II}_{1-a}M^{III}_{a}O_{b}A^{n-}_{c}\cdot zH_{2}O \qquad (II)$$

where the value of a is suitably from 0.2 to 0.4;
or formula (III):

$$M^{II}_{1-a}M^{III}_{a}(OH)_{2}A^{n-}_{c}\cdot zH_{2}O \qquad (III)$$

where $0<a<0.4$
and slurrying in water (500 ml), maintaining the material at a constant maintained pH value selected from the range between 3 to 9, preferably between 4 to 8, most preferably between 5 to 7 for 60 mins, preferably 30 mins, more preferably 15 mins or less with an acid and/or chelating agent, preferably HCl of concentration 0.01 M to 5 M, more preferably a concentration from 0.1 to 2 M, more preferably from 0.5 to 1.5 M, most preferably with 1M HCl.

The slurry is then filtered and washed with (200 ml) of water. Preferably 200 ml or more, more preferably 600 ml or more, most preferred 3000 ml or more. After the filtering or centrifuging and washing, the drying is preferably carried out at low temperature (such as providing a product temperature of up to 120° C.), for example by oven drying, spray drying or fluid bed drying. Oversize particles are then size reduced by milling and/or removed by sieving and/or any other suitable technique, for example to restrict the material to particles which are substantially no greater than 100 µm in diameter. Preferably, as measured by sieving, less than 10% by weight of particles are greater than 106 µm in diameter, more preferably less than 5%. Most preferably, no particles are greater than 106 µm in diameter as measured by sieving.

Preferably, the treatment results in a reduction in the amount of loss into solution of metal $M^{II}$ from the acid-treated compound by at least 5% by weight compared to loss from the untreated compound, when measuring the loss of metal $M^{II}$ using the test as hereinafter described.

The substances of the invention may contain at least one compound of formula (I) or formula (IV) but the process mentioned above for making the starting material may also cause other materials to be present in the intermediate product e.g. of formula (II) and/or (III) in the final product, for example single (as opposed to mixed) metal compounds which may also be formed during the co-precipitation or depletion process.

Determination of Phosphate Binding Capacity

In Vitro Phosphate Binding Test in Simple Phosphate Solutions

A specific method for determining phosphate binding capacity is given in more detail herein. This was the method actually used in the Examples. However, as a generality, elsewhere in this specification, unless specifically indicated to the contrary, any reference to percentage phosphate binding capacity is preferably that determined by the following method. 0.4 gram of the substance of the invention is added to 10 ml, 40 mmol l$^{-1}$ sodium phosphate solution adjusted to a pH of choice. Preferably, any quoted percentage phosphate binding capacity herein is maintained for measurements at pH values over the range of from 3 to 7, more preferably from 2 to 8. Samples are homogenised and gently agitated at room temperature (20° C.) for 30 minutes. Following centrifugation for 5 min at 3000 rpm, the supernatant is filtered through 0.22 µm millipore filters. Soluble phosphate is measured in the supernatant. The percentage phosphate bound by the phosphate binder is then calculated relative to the untreated phosphate starting solution.

Phosphate Binding Tests in a Model of the Human Gastro Intestinal Tract.

In vitro phosphate binding tests are widely established in the literature for the evaluation of efficacy of phosphate binders in the treatment of hyperphosphataemia. The principle of phosphate binding test is well accepted as transferable to in vivo situations. To further exemplify this we also determined the phosphate binding activity in a sophisticated gastro-intestinal model named tiny-TIM in the presence of a test meal.

Phosphate binding of the Mg depleted product of 500 mg of example A, 2 and 5 were placed in capsules (gelatine capsule) and dosed into tiny-TIM which is a model of the human gastro intestinal tract (by TNO, Zeist, The Netherlands). Details of this model have been widely published; for example as in U.S. Pat. No. 5,525,305. These experiments were performed under the average physiological conditions of the gastrointestinal tract representative for humans. These conditions include the dynamics of gastric emptying and intestinal transit times, the gastric and intestinal pH values, and the composition and activity of the secretion products. The phosphate binding capacity was determined from a reduction of bio-accessible phosphorus (fraction available for intestinal absorption).

Phosphate" refers to the total phosphate in solution. Depending on the pH of the solution, this "phosphate" can be in the form of $PO_4^{3-}$, $HPO_4^{2-}$, $H_2PO_4^{-}$ or $H_3PO_4$ Pharmaceutical Compositions A pharmaceutically acceptable carrier may be any material with which the substance of the invention is formulated to facilitate its administration. A carrier may be a solid or a liquid, including a material which is normally gaseous but which has been compressed to form a liquid, and any of the carriers normally used in formulating pharmaceutical compositions may be used. Preferably, compositions according to the invention contain 0.5% to 95% by weight of active ingredient. The term pharmaceutically acceptable carrier encompasses diluents, excipients or adjuvants.

When the substances of the invention are part of a pharmaceutical composition, they can be formulated in any suitable pharmaceutical composition form e.g. powders, granules, granulates, sachets, capsules, stick packs, battles, tablets but especially in a form suitable for oral administration for example in solid unit dose form such as tablets, capsules, or in liquid form such as liquid suspensions, especially aqueous suspensions or semi-solid formulations, e.g. gels, chewy bar, dispersing dosage, chewable dosage form or edible sachet. Direct addition to food may also be possible.

Dosage forms adapted for extra-corporeal or even intravenous administration are also possible. Suitable formulations can be produced by known methods using conventional solid carriers such as, for example, lactose, starch or talcum or liquid carriers such as, for example, water, fatty oils or liquid paraffins. Other carriers which may be used include materials derived from animal or vegetable proteins, such as the gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; polypeptide/protein or polysaccharide complexes such as gelatin-acacia complexes; sugars such as mannitol, dextrose, galactose and trehalose; cyclic sugars such as cyclodextrin; inorganic salts such as sodium phosphate, sodium chloride and aluminium silicates; and amino acids having from 2 to 12 carbon atoms such as a glycine, L-alanine, L-aspartic acid, L-glutamic acid, L-hydroxyproline, L-isoleucine, L-leucine and L-phenylalanine.

Auxiliary components such as tablet disintegrants, solubilisers, preservatives, antioxidants, surfactants, viscosity enhancers, colouring agents, flavouring agents, pH modifiers, sweeteners or taste-masking agents may also be incorporated into the composition. Suitable colouring agents include red, black and yellow iron oxides and FD & C dyes such as FD & C blue No. 2 and FD & C red No. 40 available from Ellis & Everard. Suitable flavouring agents include mint, raspberry, liquorice, orange, lemon, grapefruit, caramel, vanilla, cherry and grape flavours and combinations of these. Suitable pH modifiers include sodium hydrogencarbonate, citric acid, tartaric acid, hydrochloric acid and maleic acid. Suitable sweeteners include aspartame, acesulfame K and thaumatin. Suitable taste-masking agents include sodium hydrogencarbonate, ion-exchange resins, cyclodextrin inclusion compounds, adsorbates or microencapsulated actives.

For treatment of and prophylaxis of hyperphosphataemia, preferably amounts of from 0.1 to 500 mg, more preferably from 1 to 200, mg/kg body weight of substance of the invention as active compound are administered daily to obtain the desired results. Nevertheless, it may be necessary from time to time to depart from the amounts mentioned above, depending on the body weight of the patient, the method of application, the animal species of the patient and its individual reaction to the drug or the kind of formulation or the time or interval in which the drug is applied. In special cases, it may be sufficient to use less than the minimum amount given above, whilst in other cases the maximum dose may have to be exceeded. For a larger dose, it may be advisable to divide the dose into several smaller single doses. Ultimately, the dose will depend upon the discretion of the attendant physician. Administration soon before meals, e.g. within one hour before a meal or taken with food will usually be preferred.

A typical single solid unit dose for human adult administration may comprise from 1 mg to 1 g, preferably from 10 mg to 800 mg of substance of the invention.

A solid unit dose form may also comprise a release rate controlling additive. For example, the substance of the invention may be held within a hydrophobic polymer matrix so that it is gradually leached out of the matrix upon contact with body fluids. Alternatively, the substance of the invention may be held within a hydrophilic matrix which gradually or rapidly dissolves in the presence of body fluid. The tablet may comprise two or more layers having different release properties. The layers may be hydrophilic, hydrophobic or a mixture of hydrophilic and hydrophobic layers. Adjacent layers in a multilayer tablet may be separated by an insoluble barrier layer or hydrophilic separation layer. An insoluble barrier layer may be formed of materials used to form the insoluble casing. A hydrophilic separation layer may be formed from a material more soluble than the other layers of the tablet core so that as the separation layer dissolves the release layers of the tablet core are exposed.

Suitable release rate controlling polymers include polymethacrylates, ethylcellulose, hydroxypropylmethylcellulose, methylcellulose, hydroxyethylcellulose, hydroxypropylcellulose, sodium carboxymethylcellulose, calcium carboxymethylcellulose, acrylic acid polymer, polyethylene glycol, polyethylene oxide, carrageenan, cellulose acetate, zein etc.

Suitable materials which swell on contact with aqueous liquids include polymeric materials include from cross-linked sodium carboxymethylcellulose, cross-linked hydroxypropylcellulose, high molecular weight hydroxypropylcellulose, carboxymethylamide, potassium methacrylatedivinylbenzene copolymer, polymethylmethacrylate, cross-linked polyvinylpyrrolidone and high molecular weight polyvinylalcohols.

Solid unit dose forms comprising a substance of the invention may be packaged together in a container or presented in foil strips, blister packs or the like, e.g. marked with days of the week against respective doses, for patient guidance.

There is also a need for formulations which could improve patient compliance, for example in case of elderly or paediatric patients. A formulation in powder dose form could be either diluted in water, reconstituted or dispersed.
Combinations The compound of the present invention may be used as the sole active ingredient or in combination with another phosphate binding agent, such as sevelamer-HCL, sevelamer-carbonate, lanthanum carbonate, calcium acetate or calcium carbonate. It may also be used in combination with a calcimimetic such as cinacalet, vitamin D or calcitriol. Furthermore, it may also be used in combinations with niacin (nicotinic acid, vitamin B3) and its metabolite nicotinamide as a means of lowering phosphate levels in dialysis patients via direct inhibition of the Na—Pi-2b sodium-dependent phosphate co-transporter in the GI tract.

In a further aspect the present invention provides use of a compound of the present invention or obtained/obtainable in accordance with the present invention in the manufacture of a medicament for the prophylaxis or treatment of hyperphosphataemia.

In a further aspect the present invention the depleted compound may also be used for combinations with soluble (e.g. glucose derivatives such as sucrose) or non soluble carbohydrates (e.g. starch, dextran, dextrin). The carbohydrates may be required to prevent ageing, transformation or degradation into side-products during storage or manufacture or preventing overdrying. Overdrying may lead to loss of the phosphate binding capacity.
Uses As discussed herein the present invention provides a mixed metal compound for use as a medicament wherein the mixed metal compound is of formula (I)

$$M^{II}_{1-a}M^{III}_{a} \qquad (I)$$

wherein $M^{II}$ is at least one bivalent metal;
$M^{III}$ is at least one trivalent metal; and
$1>a>0.4$;
the compound contains at least one n-valent anion A that the compound is charge neutral.

In a further aspect the present invention provides use of a mixed metal compound in the manufacture of a medicament for binding phosphate, wherein the mixed metal compound is of formula (I)

$$M^{II}_{1-a}M^{III}_{a} \qquad (I)$$

wherein $M^{II}$ is at least one bivalent metal;
$M^{III}$ is at least one trivalent metal; and
$1>a>0.4$;
the compound contains at least one n-valent anion $A^{n-}$ such that the compound is charge neutral.

In a further aspect the present invention provides use of a mixed metal compound in the manufacture of a medicament for the prophylaxis or treatment of any one of hyperphosphataemia, renal insufficiency, hypoparathyroidism, pseudohypoparathyroidism, acute untreated acromegaly, chronic kidney disease (CKD), clinically significant changes in bone mineralisation (osteomalecia, adynamic bone disease, osteitis fibrosa), soft tissue calcification, cardiovascular disease associated with high phosphates, secondary hyperparathyroidism, over medication of phosphate salts and other conditions requiring control of phosphate absorption, wherein the mixed metal compound is of formula (I)

$$M^{II}_{1-a}M^{III}_{a} \quad (I)$$

wherein $M^{II}$ is at least one bivalent metal;
$M^{III}$ is at least one trivalent metal; and
$1 > a > 0.4$;
the compound contains at least one n-valent anion $A^{n-}$ such that the compound is charge neutral.

In a further aspect the present invention provides use of a mixed metal compound in the manufacture of a medicament for the prophylaxis or treatment of any one of hyperphosphataemia, renal insufficiency, hypoparathyroidism, pseudohypoparathyroidism, acute untreated acromegaly, chronic kidney disease and over medication of phosphate salts, wherein the mixed metal compound is of formula (I)

$$M^{II}_{1-a}M^{III}_{a} \quad (I)$$

wherein $M^{II}$ is at least one bivalent metal;
$M^{III}$ is at least one trivalent metal; and
$1 > a > 0.4$;
the compound contains at least one n-valent anion $A^{n-}$ such that the compound is charge neutral.

Preferably the compound is used in the manufacture of a medicament for the prophylaxis or treatment of hyperphosphataemia.

In a further aspect the present invention provides use of a compound of the present invention or obtained/obtainable in accordance with the present invention in the manufacture of a medicament for the prophylaxis or treatment of any one of hyperphosphataemia, renal insufficiency, hypoparathyroidism, pseudohypoparathyroidism, acute untreated acromegaly, chronic kidney disease and over medication of phosphate salts.

Examples of one or more of the symptoms which may indicate risk for the presence of CKD: a creatine concentration of above 1.6 mg/dL, a blood phosphate level of above 4.5 mg/dL, any detectable blood in urine, urine protein concentration above 100 mg/dL, a urine albumin concentration above about 100 mg/dL, a glomerular filtration rate (GFR) of below 90 mL/min/1.73 m2 or a parathyroid hormone concentration in the blood above 150 pg/mL. The symptoms are also defined by the National Kidney Foundation-Kidney Disease Outcomes Quality Initiative ("NKF-K/DOQI" or "K/DOQI,".

In one preferred aspect the chronic kidney disease (CKD) treated in accordance with the presence invention is CKD having stage one to five.

The medicament may be used on animals, preferably humans.

It should be noted that formulas (I), (II), (III) and (IV) are to be interpreted in such a way as to preserve overall charge neutrality.

The present invention will now be explained in more detail by way of the following non-limiting examples.

Figure 2:
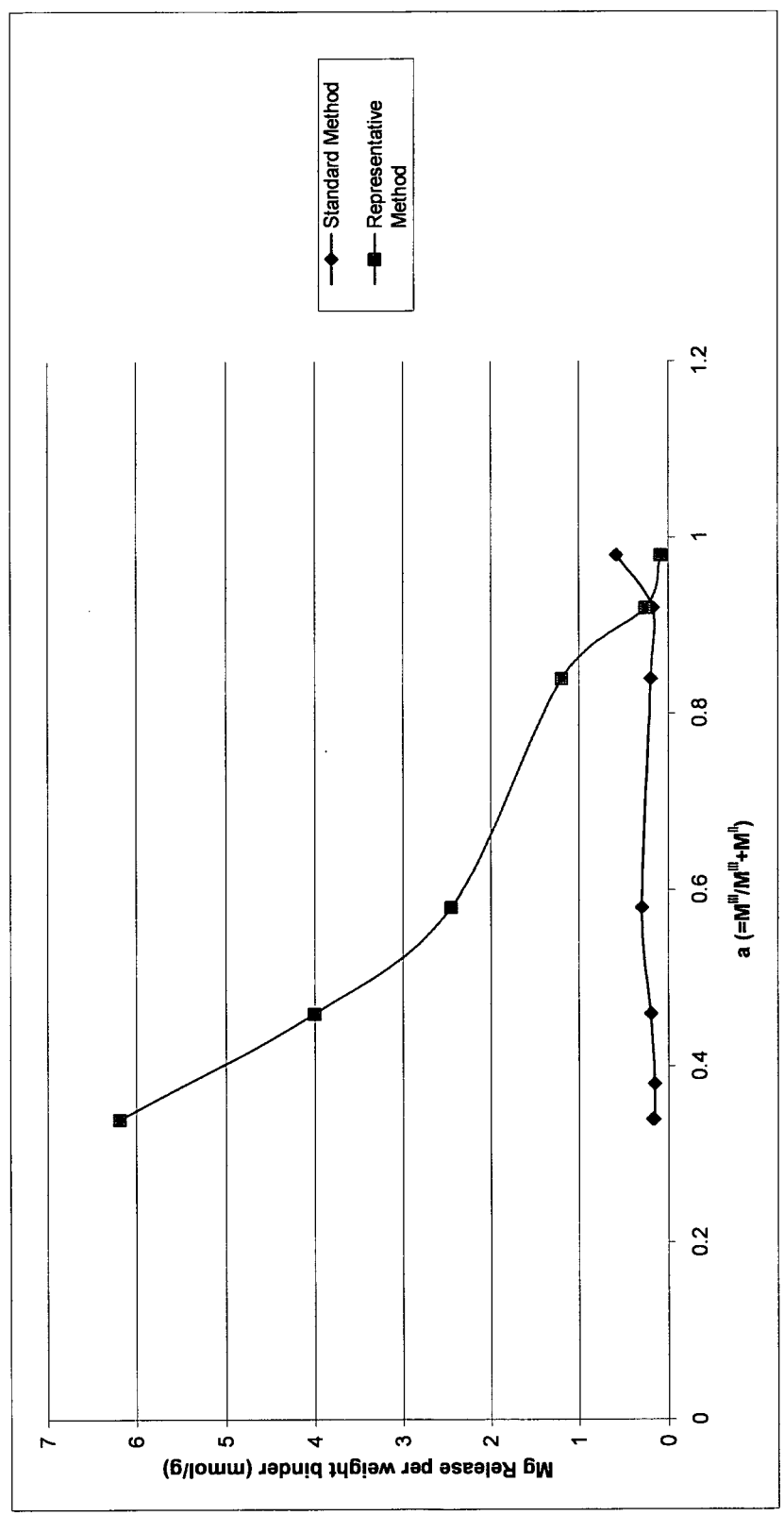

FIG. 1 shows a graph, and
FIG. 2 shows a graph.

EXAMPLES

Methods for Preparation of Compound (a) Preparation of Compounds of Formula (II) (Example B) and Compounds of Formula (III) (Example A, C, D, E, F, G) and Compounds for Comparison of Single Metal Type which can be Seen in Table 2.

Starting materials designated Examples A, C, D, E and F were prepared by the methods described in WO-A-99/15189 according to the co-precipitation route. Starting material designated Example B were prepared by the method described in PCT/GB2006/000452 as a heat-treatment at 500° C. for 3 hours.

The materials of Example A, B, C, D were targeted to have Mg:Fe ratios of 2:1 and Example E targeted to a ratio of 4:1. Example F has a Mg Al ratio targeted to a ratio of 3:1. Unless specifically mentioned elemental compositions were determined from the washed, milled and or sieved material of particle size which are substantially no greater than 100 μm in diameter. The actual molecular formulae found by analysis were:

Example A: $[Mg_{0.67}Fe_{0.33}(OH)_2][(CO_3)_{0.17}(SO_4)_{0.01}].0.43 H_2O][Na_2SO_4]_{0.03}$
Example B: $[Mg_{0.67}Fe_{0.33}O_{1.11}][(CO_3)_{0.06}.0.22H_2O]$
Example C: Example A in slurry form
Example D: Example A in wet cake form
Example E: $[Mg_{0.80}Fe_{0.20}(OH)_2][(CO_3)_{0.16}(SO_4)_{0.01}].0.60 H_2O][Na_2SO_4]_{0.03}$
Example F: $[Mg_{0.75}Al_{0.25}(OH)_2][(CO_3)_{0.13}.zH_2O]$
Example G: $[Mg_2Fe_2^{2+}Fe_2^{3+}(OH)_{12}CO_3.nH_2O]$
Example H: FeOOH (99% purity) purchased from Sigma Aldrich
Example I: $Fe_2O_3$ (99% purity) purchased from Sigma Aldrich
Example J: FeOOH (66%)/MgOH (34%) mixture
Example K: FeOOH (82%)/MgOH (18%) mixture
Example L: $Fe_2O_3$ (66%)/MgO (34%) mixture
Example M: $Fe_2O_3$ (82%)/MgO (18%) mixture
Example N: $[Mg_{0.01}Fe_{0.99}(OH)_dA^{n-}_c.zH_2O]$
Example O: $[Mg_{0.5}Fe_{0.5}(OH)_dA^{n-}_c.zH_2O]$
Example P: Fe(O)OH
Example Q: Lanthanum Carbonate Example G was prepared using the described method from WO-A-99/15189 according to the co-precipitation of Ferric Chloride, Magnesium and Ferric Sulphate salts in a 1:1:1 ratio respectively. The product was isolated by freeze drying.

Example J-K were prepared by the mixing of Fe(O)OH and MgOH hydroxides to produce products with weight % Fe(O)OH: MgOH ratios of 66:34 and 82:18. The sample were milled and or sieved to a particle size which was substantially no greater than 106 μm in diameter.

Example L-M were prepared by the mixing of $Fe_2O_3$ and MgO oxides to produce products with weight % $Fe_2O_3$:MgO ratios of 66:34 and 82:18. The sample were milled and or sieved to a particle size which was substantially no greater than 106 μm in diameter.

Starting materials designated Examples N and O were prepared by methods described in WO-A-99/15189 according to the co-precipitation route and both with an intended molar ratio of Mg:Fe=1:1 i.e. the salts of Ferric Sulphate and Mg Sulphate were co-precipitated in a 1:1 molar ratio. Example N was prepared from precipitation at pH 5 and Example O was prepared from precipitation at pH 10. Starting material designated P was synthesised using the Fe(O)OH method as described in WO 2008/071747 A1.

Material Q was prepared from commercially available Fosrenol (La carbonate). The material was milled and or sieved to a particle size which was substantially no greater than 106 μm in diameter.

(b) Preparation of Compounds of Formula (I) or (IV)

Actual preparation of depleted compound according to M1 (of Table 1) was as follows.

After taking 20 g of starting material (either one of compound Example A to E) and slurrying in 500 ml water, pH was immediately measured and the pH maintained constant at pH 3 for 30 minutes by addition of 1 M HCl (the depleting agent). The slurry obtained was then filtered and washed with 200 ml water and then dried in an oven (at 120° C. for 3 hrs). Oversize particles were then removed by milling and sieving to a particle size of no greater than 106 μm in diameter by sieving. The depletion method of M1 was then varied in that they were conducted using different depleting agents, at different strengths, for different treatment periods, and at different preparation pH.

The depleting agents were selected from HCl, $H_2SO_4$, citric acid, EDTA, $HNO_3$, acetic acid; the molarity of HCl was also selected from 1M and 5M. The reaction media was selected from water or aqueous phosphate solution. The contact time during acid addition was selected from 15 minutes or 30 minutes or 60 minutes. The preparation pH was selected from 3, 4, 5, 6, 7, 8, or 9.

The methods are shown below in Table 1.

TABLE 1

Methods of Depletion

| Method Number M0 | Reaction media no treatment | Depletion agent | Reaction Time | Flow of addition depletion agent | Wash water | Oven Drying temp | Oven drying Time | % Slurry | Slurry Aged or unaged | Reaction pH |
|---|---|---|---|---|---|---|---|---|---|---|
| M1 | water | 1 M HCl | 30 | Variable[i] | 200 ml | 120° C. | 3 hrs | 4 | unaged | 3 |
| M2 | water | 1 M HCl | 30 | Variable[i] | 200 ml | 120° C. | 3 hrs | 4 | unaged | 4 |
| M3 | water | 1 M HCl | 30 | Variable[i] | 200 ml | 120° C. | 3 hrs | 4 | unaged | 5 |
| M4 | water | 1 M HCl | 30 | Variable[i] | 200 ml | 120° C. | 3 hrs | 4 | unaged | 6 |
| M5 | water | 1 M HCl | 30 | Variable[i] | 200 ml | 120° C. | 3 hrs | 4 | unaged | 7 |
| M6 | water | 1 M HCl | 30 | Variable[i] | 200 ml | 120° C. | 3 hrs | 4 | unaged | 8 |
| M7 | water | 1 M HCl | 30 | Variable[i] | 200 ml | 120° C. | 3 hrs | 4 | unaged | 9 |
| M8 | water | 1 M HCl | 15 | Variable[i] | 200 ml | 120° C. | 3 hrs | 4 | unaged | 3 |
| M9 | water | 1 M HCl | 15 | Variable[i] | 200 ml | 120° C. | 3 hrs | 4 | unaged | 4 |
| M10 | water | 1 M HCl | 15 | Variable[i] | 200 ml | 120° C. | 3 hrs | 4 | unaged | 5 |
| M11 | water | 1 M HCl | 15 | Variable[i] | 200 ml | 120° C. | 3 hrs | 4 | unaged | 6 |
| M12 | water | 1 M HCl | 15 | Variable[i] | 200 ml | 120° C. | 3 hrs | 4 | unaged | 8 |
| M13 | water | 1 M HCl | 60 | Variable[i] | 200 ml | 120° C. | 3 hrs | 4 | unaged | 3 |
| M14 | water | 1 M HCl | 60 | Variable[i] | 200 ml | 120° C. | 3 hrs | 4 | unaged | 4 |
| M15 | water | 1 M HCl | 60 | Variable[i] | 200 ml | 120° C. | 3 hrs | 4 | unaged | 5 |
| M16 | water | 1 M HCl | 60 | Variable[i] | 200 ml | 120° C. | 3 hrs | 4 | unaged | 6 |
| M17 | water | 1 M HCl | 60 | Variable[i] | 200 ml | 120° C. | 3 hrs | 4 | unaged | 8 |
| M18 | phosphate | 1 M HCl | 30 | Variable[i] | 200 ml | 120° C. | 3 hrs | 4 | unaged | 3 |
| M19 | phosphate | 1 M HCl | 30 | Variable[i] | 200 ml | 120° C. | 3 hrs | 4 | unaged | 4 |
| M20 | phosphate | 1 M HCl | 30 | Variable[i] | 200 ml | 120° C. | 3 hrs | 4 | unaged | 5 |
| M21 | phosphate | 1 M HCl | 30 | Variable[i] | 200 ml | 120° C. | 3 hrs | 4 | unaged | 6 |
| M22 | phosphate | 1 M HCl | 30 | Variable[i] | 200 ml | 120° C. | 3 hrs | 4 | unaged | 7 |
| M23 | phosphate | 1 M HCl | 30 | Variable[i] | 200 ml | 120° C. | 3 hrs | 4 | unaged | 8 |
| M24 | phosphate | 1 M HCl | 30 | Variable[i] | 200 ml | 120° C. | 3 hrs | 4 | unaged | 9 |
| M25 | water | 5 M HCl | 30 | Variable[i] | 200 ml | 120° C. | 3 hrs | 4 | unaged | 4 |
| M26 | water | 5 M HCl | 30 | Variable[i] | 200 ml | 120° C. | 3 hrs | 4 | unaged | 5 |
| M27 | water | 5 M HCl | 30 | Variable[i] | 200 ml | 120° C. | 3 hrs | 4 | unaged | 6 |
| M28 | water | 5 M HCl | 30 | Variable[i] | 200 ml | 120° C. | 3 hrs | 4 | unaged | 7 |
| M29 | water | 5 M HCl | 30 | Variable[i] | 200 ml | 120° C. | 3 hrs | 4 | unaged | 8 |
| M30 | water | 1M | 30 | Variable[i] | 200 ml | 120° C. | 3 hrs | 4 | unaged | 5 |
| M31 | water | 1M | 30 | Variable[i] | 200 ml | 120° C. | 3 hrs | 4 | unaged | 6 |
| M32 | water | 1M | 30 | Variable[i] | 200 ml | 120° C. | 3 hrs | 4 | unaged | 8 |
| M33 | water | 1M Citric | 30 | Variable[i] | 200 ml | 120° C. | 3 hrs | 4 | unaged | 6 |
| M34 | water | 1M Citric | 30 | Variable[i] | 200 ml | 120° C. | 3 hrs | 4 | unaged | 8 |
| M35 | water | EDTA | 30 | Variable[i] | 200 ml | 120° C. | 3 hrs | 4 | unaged | 8 |
| M36 | water | EDTA & HCl | 30 | Variable[i] | 200 ml | 120° C. | 3 hrs | 4 | unaged | 3 |
| M37 | water | EDTA & HCl | 30 | Variable[i] | 200 ml | 120° C. | 3 hrs | 4 | unaged | 6 |
| M38 | water | HNO3 | 30 | Variable[i] | 200 ml | 120° C. | 3 hrs | 4 | unaged | 5 |
| M39 | water | HNO3 | 30 | Variable[i] | 200 ml | 120° C. | 3 hrs | 4 | unaged | 6 |
| M40 | water | HNO3 | 30 | Variable[i] | 200 ml | 120° C. | 3 hrs | 4 | unaged | 8 |
| M41 | water | 1 M | 30 | Variable[i] | 200 ml | 120° C. | 3 hrs | 4 | unaged | 6 |
| M42 | water | 1 M | 30 | Variable[i] | 200 ml | 120° C. | 3 hrs | 4 | unaged | 8 |
| M43 | water | 1 M HCl | 30 | Variable[i] | 3 L | 120° C. | 3 hrs | 12 | unaged | 3 |
| M44 | water | 1 M HCl | 30 | Variable[i] | 3 L | 120° C. | 3 hrs | 12 | unaged | 4 |
| M45 | water | 1 M HCl | 30 | Variable[i] | 3 L | 120° C. | 3 hrs | 12 | unaged | 5 |
| M46 | water | 1 M HCl | 30 | Variable[i] | 3 L | 120° C. | 3 hrs | 12 | unaged | 7 |
| M47 | water | 1 M HCl | 30 | Variable[i] | 3 L | 40° C. | 1.5 | 12 | unaged | 4 |
| M48 | water | 1 M HCl | 30 | Variable[i] | 3 L | 40° C. | 3 hrs | 12 | unaged | 4 |
| M49 | water | 1 M HCl | 30 | Variable[i] | 3 L | 40° C. | 4 hrs | 12 | unaged | 4 |
| M50 | water | 1 M HCl | 30 | Variable[i] | 3 L | 80° C. | 1.5 | 12 | unaged | 4 |
| M51 | water | 1 M HCl | 30 | Variable[i] | 3 L | 80° C. | 3 hrs | 12 | unaged | 4 |
| M52 | water | 1 M HCl | 30 | Variable[i] | 3 L | 80° C. | 4 hrs | 12 | unaged | 4 |
| M53 | water | 1 M HCl | 30 | Variable[i] | 3 L | 120° C. | 1.5 | 12 | unaged | 4 |
| M54 | water | 1 M HCl | 30 | Variable[i] | 3 L | 120° C. | 3 hrs | 12 | unaged | 4 |
| M55 | water | 1 M HCl | 30 | Variable[i] | 3 L | 120° C. | 4 hrs | 12 | unaged | 4 |

TABLE 1-continued

Methods of Depletion

| Method Number M0 | Reaction media no treatment | Depletion agent | Reaction Time | Flow of addition depletion agent | Wash water | Oven Drying temp | Oven drying Time | % Slurry | Slurry Aged or unaged | Reaction pH |
|---|---|---|---|---|---|---|---|---|---|---|
| M56 | water | 1 M HCl | 30 | Total[(ii)] | 3 L | 40° C. | 3 hrs | 12 | unaged | 4 |
| M57 | water | 1 M HCl | 30 | Slow[(iii)] | 3 L | 40° C. | 3 hrs | 12 | unaged | 4 |

[(i)]For a depletion pH less than 6, 90% of the depletion agent was added in the first 10 minutes, the remainder over 20 minutes, for a depletion pH greater than 6, 75% of the depletion agent was added in the first 5 minutes and the remainder over 25 minutes.
[(ii)]Addition of fixed amount of depletion agent at time 0 to attain desired pH
[(iii)]Addition rate 10 ml/min for first 40 minutes then 5 ml/min for additional 20 mins then 2.5 ml/min for remaining 10 minutes, total addition time 70 mins The acid-treated materials thus obtained from the various methods were then tested for phosphate binding capacity, soluble magnesium, surface absorbed water content and also subjected to X-ray diffraction analysis. The methods employed are described below.

The labelling of each method, e.g. M1, is used in the tests below to identify the particular method of depletion used for each sample.

Method for Preparation of Tablet Formulation of Depleted Compound

A dry blend comprising 80.00% w/w of the depleted compound of example 2 (Table 2), 15.00% w/w pre-gelled starch and 5.00% w/w micronized crospovidone was made in a mixer/blender, then purified water added until granulation of the blend was achieved. Any further batches of granule required from the same API were made and combined before drying. The granule was then dried in a fluid bed drier to a target moisture of 5-7% w/w then milled in a high speed blade mill until it passed through a 425 micron aperture sieve. The sieved granule was then mixed with 0.25% w/w of sieved magnesium stearate to produce the material for tabletting.

Tablets were made where possible on a Manesty F3 single station press using a double convex oblong punch and die set. Target hardness for the tablets was 10-15 Kg as measured on a Holland C50 tablet hardness tester.

Coating of the tablets was achieved using a hand held spray gun with the tablet cores in a rotating basket with the hot air for drying the tablets supplied by a hot air gun.

The coating suspension comprised: 84.03% w/w water, 0.81% w/w sodium dodecyl sulphate, 8.075% w/w Eudragit EPO, 1.21% w/w stearic acid, 2.09% w/w talc, 2.8285w/w magnesium stearate, 0.643% w/w titanium dioxide and 0.323% w/w iron oxide. The weights of coating achieved ranged from 4.0 to 6.66% w/w based on the uncoated tablet weight. The disintegration times of the coated tablets were not determined. Phosphate binding and magnesium release (standard method) was respectively 0.54 mmol/g and 0.157 mmol/g for the tablet containing the depleted compound of example 2 whereas the tablet containing the un-depleted compound showed respectively phosphate binding and magnesium release of 0.63 mmol/g and 0.16 mmol/g.

Test Method 1:
(a) Determination of Phosphate Binding Capacity and Soluble Magnesium/Iron Using Standard Method 40 mM Sodium Phosphate solution (pH 4) was prepared and treated with the phosphate-binder. The supernatant of the centrifuged phosphate-solution and binder mixture was then diluted and analysed by ICP-OES for Fe, Mg and P content. The latter analysis technique is well known to those skilled in the art. ICP-OES is the acronym for inductively coupled plasma optical emission spectroscopy.

Reagents used for this method were: Sodium Dihydrogen Phosphate Monohydrate (Aldrich), 1M hydrochloric acid, AnalaR™ water, standard phosphorous solution (10.000 µg/ml, Romil Ltd), standard magnesium solution (10,000 µg/ml, Romil Ltd), standard iron solution (1.000 µg/ml), sodium chloride (BDH).

Specific apparatus used were centrifuge (Metler 2000E), blood-tube rotator (Stuart Scientific), minishaker (MS1), ICP-OES, blood collection tubes.

Phosphate buffer (pH=4) was prepared by weighing 5.520 g (+/−0.001 g) of sodium di-hydrogen phosphate followed by addition of AnalaR™ water and transferring to a 1 ltr volumetric flask.

To the 1 ltr volumetric flask was then added 1 M HCl drop-wise to adjust the pH to pH 4 (+/−0.1) mixing between additions. The volume was then accurately made up to 1 ltr using AnalaR™ water and mixed thoroughly.

0.4 g (+/−0.005 g) of each sample was weighed into the supplied blood collection tubes and placed in the holding rack. All samples were prepared in duplicate and temperature of solutions maintained at 20° C. 10 ml aliquots of the phosphate buffer were pipetted into each of the blood collection tubes containing the pre-weighed test materials and the screw cap fitted. The vessels were agitated over a minishaker for about ten seconds. The vessels were transferred onto a blood tube rotator and mixed for 30 minutes (+/−2 minutes). The vessels were then centrifuged at 3000 rpm and 20° C. for 5 minutes. The samples were removed from the centrifuge and 2.5 ml aliquots were pipetted of the supernatant and transferred into a fresh blood collection tubes. 7.5 ml of AnalaR™ water were pipetted to each 2.5 ml aliquot and the screw cap fitted and mixed thoroughly. The solutions were then analysed on a calibrated ICP-OES.

The phosphate binding capacity was determined by:

$$\text{Phosphate binding(mmol/g)} = [S_P(\text{mmol/l}) - T_P(\text{mmol/l})]/W(\text{g/l})$$

where:
$T_P$=Analyte value for phosphate in the phosphate solution after reaction with phosphate binder=solution P (mg/l)*4/30.97. $T_P$ used in test method 1a and $T_P^1$ used instead of $T_P$ for test method 1b, 1c and 1d
$S_P$=Analyte value for phosphate in the phosphate solution before reaction with phosphate binder.
W=concentration binder (g/l) used in test method (i.e. 0.4 g/10 ml in test method 1a=40 g/l)

Magnesium release was determined by:

$$\text{Magnesium release(mmol/g)} = [T_{Mg}(\text{mmol/l}) - S_{Mg}(\text{mmol/l})]/W(\text{g/l})$$

where:
$T_{Mg}$=Analyte value for magnesium in the phosphate solution after reaction with phosphate binder=solution Mg (mg/l)*4/

24.31. $T_{Mg}$ used in test method 1a and $T_{Mg}^1$ used instead of $T_{Mg}$ for test method 1b, 1c and 1d
$S_{Mg}$=Analyte value for magnesium in the phosphate solution before reaction with phosphate binder.

Iron release was determined by:

Iron release(mmol/g)=[$T_{Fe}$(mmol/l)−$S_{Fe}$(mmol/l)]/$W$(g/l)

where:
$T_{Fe}$=Analyte value for iron in the phosphate solution after reaction with phosphate binder=solution Fe (mg/l)*4/55.85. $T_{Fe}$ used in test method 1a and $T_{Fe}^1$ used instead of $T_{Fe}$ for test method 1b, 1c and 1d
$S_{Fe}$=Analyte value for iron in the phosphate solution before reaction with phosphate binder.

The results for phosphate binding capacity, magnesium release and iron release measured by the standard method can be seen in Table 2, 3 and 4

(b) Determination of Phosphate Binding Capacity and Soluble Magnesium/Iron Using Representative Method at 0.4 g Phosphate Binder/10 ml.

The standard phosphate binding test Test Method 1 (a) involves the use of phosphate buffer adjusted to pH 4. The pH of this test was found to increase from pH 4 to approx 8.5-9 after addition of the mixed metal compounds of Examples A to F. We therefore also determined the phosphate binding capacity using a more representative method of conditions under gastric conditions (lower pH value of 3) and by maintaining the pH at a constant value by the addition of 1M HCl during the phosphate binding contrary to the standard phosphate binding test where the pH was allowed to rise during the phosphate binding.

The representative method (for measuring phosphate binding and magnesium- or iron-release) was maintained as per standard phosphate binding test Test Method 1 (a), i.e. 0.4 g of the phosphate binder was dispersed in 10 ml phosphate buffer. The temperature of solutions was 20° C. In order to monitor the pH, the sample was weighed into a Sterlin Jar. This jar is placed on a stirrer plate with stirrer placed in jar. The 10 ml of the phosphate buffer is added to the sample and the pH hereafter immediately monitored via a pH probe during 30 minutes and the pH was maintained at pH=3 using 1M HCl delivered via a Dosimat titrator. The total volume of acid added for pH adjustment never exceeded 61% of the total volume. The volume of acid used for pH adjustment in the representative method is listed below for Example 1-5 (depleted) and Example A (=starting material i.e. not depleted). For other compounds the volume of acid required to maintain the pH constant was also recorded during the phosphate binding test and used for the formula described hereinafter whereby the analyte concentration is corrected for the dilution resulting from the acid addition.

| Example Number | V volume (ml) of 1 M HCl acid used for pH adjustment in the representative method |
|---|---|
| 1 | 0 |
| 2 | 0.5 |
| 3 | 1.0 |
| 6 | 5.7 |
| A | 6.1 |

It is obvious from this data that more pH adjustment was required for these samples which had been depleted at higher pH.

The phosphate binding and Mg- and Fe-release data of the representative method was then corrected for the dilution of phosphate or compound concentration due to acid addition (as phosphate binding and Mg- and Fe-release are measured from the difference between before and after the phosphate binding reaction) using the following formula:

$$T_P^1 = T_P * (10\ ml + V)/10\ ml$$

$$T_{Mg}^1 = T_{Mg} * (10\ ml + V)/10\ ml$$

$$T_{Fe}^1 = T_{Fe} * (10\ ml + V)/10\ ml$$

Wherein $T_P$=analyte concentration for phosphate after reaction with phosphate binder
$T_P^1$=identical as $T_P$ but with concentration corrected for dilution because of acid addition
$T_{Mg}$=analyte concentration for magnesium after reaction with phosphate binder
$T_{Mg}^1$=identical as $T_{Mg}$ but with concentration corrected for dilution because of acid addition
$T_{Fe}$=analyte concentration for iron after reaction with phosphate binder
$T_{Fe}^1$=identical as $T_{Fe}$ but with concentration corrected for dilution because of acid addition After the 30 minutes phosphate binding, the slurry is transferred to a blood sample tube (approx 10 ml) and centrifuged for 5 minutes at 3000 RPM. Then as per standard phosphate binding Test Method 1 (a) 2.5 ml of the supernatant is diluted to 10 ml with AnalaR water in a separate collection tube, ready for analysis on the ICP.

The results for phosphate binding capacity, magnesium release and iron release measured with the representative method can be seen in Table 2 and 3.

c) Determination of Phosphate Binding Capacity and Soluble Magnesium/Iron Using Representative Method at 0.2 q Phosphate Binder/10 ml.

Identical method to that described in method 1b but with 0.2 g phosphate binder/10 ml Test Method 2: X-Ray Diffraction (XRD) Measurements Data was collected for fine particulate samples from 2-70° 2θ on a Philips automatic powder X-ray diffractometer using Copper K alpha radiation generated at 40 kV and 55 mA.

The results of the XRD measurements are seen in Table 3 and 5.

Test Method 3: Carbon Content Analysis by the Leco Method

This method was used to determine the levels of carbon content (indicative of the presence of the carbonate anion present in the mixed metal compound) A sample of known mass is combusted at around 1350° C. in a furnace in a pure oxygen atmosphere. Any carbon in the sample is converted to $CO_2$ which is passed through a moisture trap before being measured by an infra-red detector. By comparing against a standard of known concentration, the carbon content of the sample can be found. A Leco SC-144DR carbon and Sulphur Analyser, with oxygen supply, ceramic combustion boats, boat lance and tongs was used. 0.2 g (+/−0.01 g) of sample was weighed into a combustion boat. The boat was then placed into the Leco furnace and the carbon content analysed. The analysis was performed in duplicate.

The % C was determined by:

$$\%\ C(sample) = (\%\ C_1 + \%\ C_2)/2$$

Where $C_1$ and $C_2$ are individual carbon results.

The results of the carbon content measurements are seen in Table 5 and were expressed as % $CO_2$=% C×44/12

Test Method 4: XRF Analysis

XRF analysis of the product was performed by using a Philips PW2400 Wavelength Dispersive XRF Spectrometer. The sample was fused with 50:50 lithium tetra/metaborate (high purity) and presented to the instrument as a glass bead. All reagents used were analytical grade or equivalent unless specified. AnalaR™ water, Lithium tetraborate 50% metaborate 50% flux (high purity grade ICPH Fluore-X 50). A muffle furnace capable of 1025° C., extended tongs, hand tongs, Pt/5% Au casting tray and Pt/5%/Au dish were used. 1.5 g (+/−0.0002 g) of sample and 7.5000 g (+/−0.0002 g) of tetra/metaborate was accurately weighed out into a Pt/5%/Au dish. The two constituents were lightly mixed in the dish using a spatula, prior to placement in the furnace preset to 1025° C. for 12 minutes. The dish was agitated at 6 minutes and 9 minutes to ensure homogeneity of the sample. Also at 9 minutes the casting tray was placed in the furnace to allow for temperature equilibration. After 12 minutes the molten sample was poured into the casting tray, which was removed from the furnace and allowed to cool. The bead composition was determined using the spectrophotometer.

The results of the XRF measurements are seen in Table 5.

Test Method 5: Determination of a, b, c, d and z Values

Value d of formula $[M^{II}_{(1-a)}M^{III}_{(a)}O_b(OH)_d A^{n-}_{c} \cdot zH_2O]$ is an indicator for the relative amount of hydroxy (OH) groups and was determined from the titration of the un-depleted compound with HCl acid (i.e. by measuring the amount of acid required to change the pH from the initial pH (approx 9 for the Mg Fe mixed metal compound A; of before depletion) to the final pH (pH after depletion and pH at which the depleted compound was isolated). The value for d was found to correlate with the pH buffering properties of the compound. For example, the max value for d of 2 can be found for the un-depleted compound of the following composition: $[Mg_{0.67}Fe_{0.33}(OH)_2][CO_3)_{0.17}(SO_4)_{0.01} \cdot 0.43H_2O]$ $[Na_2SO_4]_{0.03}$. Titrating this compound with acid will result in release of magnesium and hydroxy ions; the released hydroxy ions in turn result in pH buffering.

The following formula was used to calculate d $d = 2 \times [((\text{volume of acid required to deplete material to pH 3}) - (\text{volume of acid}))/(\text{volume of acid required to deplete material to pH 3})$ The results shown below are an example of the variation of d as a function of pH after depletion of example A,

| a | pH | Volume of acid (ml) | d |
|---|---|---|---|
| 0.98 | 3 | 115 | 0.00 |
| 0.95 | 4 | 89 | 0.45 |
| 0.84 | 5 | 53 | 1.08 |
| 0.58 | 6 | 22 | 1.62 |
| 0.46 | 7 | 4.9 | 1.91 |
| 0.38 | 8 | 1.8 | 1.97 |
| 0.36 | 9 | 0 | 2.00 | the value of b was determined by the need for charge neutrality as expressed by the formula $2+a-2b-d-cn=0$; the value for a was determined from the ratio between the divalent and trivalent metal content according to formula $$a = \frac{\text{number of moles of } M^{III}}{(\text{number of moles of } M^{II} + \text{number of moles of } M^{III})};$$

The number of moles of $M^{III}$ and $M^{II}$ was determined by the XRF method.

The value for c (anion) was determined from the Leco ($CO_2$) and XRF ($SO_3$) method:

$$= \frac{\left(\begin{array}{c}(\% \, CO_2/\text{molecular weight of } CO_2) + \\ (\% \, SO_3/\text{molecular weight of } SO_3)\end{array}\right)}{(2 \times (\% \, Fe_2O_3/\text{molecular weight of } Fe_2O_3))}$$

z was calculated by $$= \frac{\left(\begin{array}{c}(a = M^{III}/M^{III} + M^{II}) \times \\ (\% \, H_2O/\text{molecular weight of } H_2O)\end{array}\right)}{(2 \times (\% \, Fe_2O_3/\text{molecular weight of } Fe_2O_3))}$$

% $H_2O$ was determined from % w/w $H_2O = 100 - (\%$ w/w $M^{II}O + \%$ w/w $M^{III}_2O_3 + \%$ w/w $CO_2 + \%$ w/w $Na_2O + \%$ w/w $SO_3)$ Test Method 6 EXAF Studies Data were collected at the Fe K-edge at ambient temperature in transmission (standards) mode on station 9.3 of the Daresbury Synchrotron Radiation Source, operating at 2 GeV with an average current of 180 mA. A Si(III) double crystal monochromator was used, detuned to reject 50% of the incident signal in order to minimise harmonic contamination. The monochromator angle was calibrated by running an edge scan for the Fe foil standard. Io and It were measured using ion chambers filled with a mixture of Ar/He. One scan was recorded for each of the transmission standards and sample.

The data were initially processed using the Daresbury program EXCALIB, to convert the monochromator angles to the corresponding X-ray energy; for transmission spectra the signal was calculated as ln(Io/It). The spectra collected for each sample were compared and summed.

TABLE 2

Formula Constants & All Analysis Results

| Example Number | Mixed Metal Compounds | Method of depletion | Formula Constants $[M^{II}_{(1-a)}M^{III}_{(a)}O_b(OH)_d A^{n-}_{c} \cdot zH_2O]$ | | | | | | Phosphate bound Standard method (1a) mmol/g | Mg release mmol/g | Fe release µmol/g | Phosphate bound Representative method (1b)µ mmol/g | Mg release mmol/g | Fe release µmol/g |
|---|---|---|---|---|---|---|---|---|---|---|---|---|---|---|
| | | | a (=$M^{III}$/$M^{III}$+$M^{II}$) | b | c | d | Z | cn/a | | | | | | |
| Starting or reference materials | | | | | | | | | | | | | | |
| A | $Mg_2Fe$ | M0 | 0.34 | 0.03 | 0.15 | 2.00 | 1.65 | 0.86 | 0.71 | 0.17 | 0.00 | 0.99 | 6.18 | 0.02 |
| B | $Mg_2Fe$ calcined | M0 | 0.33 | 1.11 | 0.02 | 0 | 0.22 | 0.11 | 0.84 | 0.01 | 0.00 | 1.02 | 9.08 | 0.00 |
| C | $Mg_2Fe$ slurry | M0 | | | | | | | 0.83 | 0.19 | 0.00 | | | |
| D | $Mg_2Fe$ wet cake | M0 | 0.34 | 0.26 | 0.04 | 2.00 | 1.87 | 0.23 | 0.79 | 0.11 | 0.00 | 1.00 | 6.94 | 0.02 |
| E | $Mg_4Fe$ | M0 | 0.20 | | 0.05 | | 1.89 | 0.53 | 0.87 | 0.06 | 0.00 | 0.99 | 2.26 | 0.03 |
| F | $Mg_3Al$ | M0 | 0.25 | | 0.05 | | 5.20 | 0.18 | 1.34 | 0.05 | 0.00 | 0.45 | 3.58 | 0.00 |
| G | $Mg^{II}Fe^{II}Fe^{III}$ | M0 | 0.62 | | 0.04 | | 4.92 | 0.14 | 0.44 | 0.17 | 0.00 | | | |

TABLE 2-continued

Formula Constants & All Analysis Results

| Example Number | Mixed Metal Compounds | Method of depletion | Formula Constants $[M^{II}_{(1-a)}M^{III}_{(a)}O_b(OH)_d A^{n-}_c \cdot zH_2O]$ a (=$M^{III}$/ $M^{III}+M^{II}$) | b | c | d | Z | cn/a | Phosphate bound Standard method (1a) mmol/g | Mg release mmol/g | Fe release µmol/g | Phosphate bound Representative method (1b) mmol/g | Mg release mmol/g | Fe release µmol/g |
|---|---|---|---|---|---|---|---|---|---|---|---|---|---|---|
| H | FeOOH (Sigma) | M0 | 1.00 | 1.00 | 0.00 | 1.00 | | | 0.24 | 0.00 | 0.00 | 0.81 | 0.05 | 0.00 |
| I | Fe2O3 (Sigma) | M0 | 1.00 | 1.50 | 0.00 | 0.00 | | | 0.01 | 0.00 | 0.00 | 0.05 | 0.00 | 0.00 |
| J | FeOOH/MgOH mix | M0 | 0.50 | 0.50 | 0.00 | | | | 0.78 | 0.00 | 0.00 | 0.54 | 7.31 | 0.00 |
| K | FeOOH/MgOH mix | M0 | 0.70 | 0.70 | 0.00 | | | | 0.763 | 0.00 | 0.00 | 0.62 | 4.01 | 0.00 |
| L | Fe2O3/MgO mix | M0 | 0.48 | 0.48 | 0.00 | | | | 0.664 | 0.01 | 0.00 | 0.07 | 7.56 | 0.00 |
| M | Fe2O3/MgO mix | M0 | 0.69 | 0.69 | 0.00 | | | | 0.627 | 0.01 | 0.00 | 0.05 | 5.86 | 0.00 |
| N | MgFe pH5 prec. | M0 | 0.99 | 1.00 | | | | | 0.76 | 0.01 | 0.00 | 0.94 | 0.01 | 0.00 |
| O | MgFe pH10 prec. | M0 | 0.52 | 0.52 | | | | | 0.69 | 0.12 | 0.00 | 0.98 | 4.60 | 0.00 |
| P | FeOOH (prec) | M0 | 1.00 | 0.98 | | | | | 0.52 | 0.00 | 3.73 | 0.91 | 0.02 | 0.00 |
| Q | Lacarbonate | M0 | 1.00 | | | | | | 0.13 | 0.01 | 0.00 | | | |
| | Mg-depleted materials | | | | | | | | | | | | | |
| 1 | A | M1 | 0.98 | 1.48 | 0.01 | 0.00 | 2.64 | 0.02 | 0.65 | 0.58 | 0.00 | 0.25 | 0.08 | 0.72 |
| 2 | A | M2 | 0.92 | 1.24 | 0.01 | 0.49 | 2.05 | 0.02 | 0.84 | 0.17 | 0.00 | 0.86 | 0.25 | 0.21 |
| 3 | A | M3 | 0.84 | 0.87 | 0.01 | 1.08 | 2.01 | 0.02 | 0.81 | 0.19 | 0.00 | 0.90 | 1.19 | 1.03 |
| 4 | A | M4 | 0.58 | 0.35 | 0.13 | 1.62 | 1.49 | 0.45 | 0.86 | 0.29 | 0.00 | 1.02 | 4.66 | 0.00 |
| 5 | A | M5 | 0.46 | 1.27 | 0.14 | 0.92 | 1.60 | 0.61 | 0.75 | 0.19 | 0.00 | 1.02 | 3.98 | 0.00 |
| 6 | A | M6 | 0.38 | | | 1.97 | | | 0.64 | 0.15 | 0.00 | | | |
| 7 | A | M7 | 0.34 | 0.03 | 0.15 | 2.00 | 1.65 | 0.88 | 0.60 | 0.16 | 0.00 | | | |
| 8 | A | M8 | | | | | | | 0.90 | 0.41 | 0.00 | | | |
| 9 | A | M9 | | | | | | | 0.77 | 0.64 | 0.00 | | | |
| 10 | A | M10 | | | | | | | 0.73 | 0.10 | 0.00 | | | |
| 11 | A | M11 | 0.49 | | 0.13 | | 1.45 | 0.52 | 0.74 | 0.13 | 0.00 | | | |
| 12 | A | M12 | | | | | | | 0.60 | 0.20 | 0.00 | | | |
| 13 | A | M13 | | | | | | | 0.78 | 0.43 | 0.00 | | | |
| 14 | A | M14 | | | | | | | 0.69 | 0.58 | 0.00 | | | |
| 15 | A | M15 | | | | | | | 0.69 | 0.47 | 0.00 | | | |
| 16 | A | M16 | 0.66 | | 0.09 | | 1.34 | 0.28 | 0.76 | 0.15 | 0.00 | | | |
| 17 | A | M17 | | | | | | | 0.59 | 0.20 | 0.00 | | | |
| 18 | A | M18 | 0.98 | | | | | | 0.67 | 0.06 | 0.00 | | | |
| 19 | A | M19 | 0.92 | | | | | | 0.67 | 0.20 | 0.00 | | | |
| 20 | A | M20 | 0.75 | | | | | | 0.60 | 0.22 | 0.00 | | | |
| 21 | A | M21 | 0.46 | | | | | | 0.52 | 0.20 | 0.00 | | | |
| 22 | A | M22 | 0.35 | 0.19 | 0.03 | 1.91 | 2.19 | 0.19 | | | | 1.02 | 6.99 | 0.02 |
| 23 | A | M23 | 0.35 | 0.15 | 0.03 | 1.97 | 2.30 | 0.20 | | | | 1.02 | 6.79 | 0.04 |
| 24 | A | M24 | 0.34 | 0.14 | 0.04 | 2.00 | 2.11 | 0.21 | | | | 1.00 | 4.31 | 0.23 |
| 25 | A | M25 | | | | | | | 0.74 | 0.68 | 0.00 | | | |
| 26 | A | M26 | | | | | | | 0.75 | 0.72 | 0.00 | | | |
| 27 | A | M27 | | | | | | | 0.87 | 0.51 | 0.00 | | | |
| 28 | A | M28 | | | | | | | 0.73 | 0.22 | 0.00 | | | |
| 29 | A | M29 | | | | | | | 0.63 | 0.22 | 0.00 | | | |
| 30 | A | M30 | | | | | | | 0.51 | 0.73 | 0.00 | | | |
| 31 | A | M31 | | | | | | | 0.71 | 0.16 | 0.00 | | | |
| 32 | A | M32 | | | | | | | 0.51 | 0.23 | 0.00 | | | |
| 33 | A | M33 | | | | | | | Depletion not successful | | | | | |
| 34 | A | M34 | | | | | | | 0.57 | 0.24 | 5.34 | | | |
| 35 | A | M35 | | | | | | | 0.64 | 0.26 | 5.47 | | | |
| 36 | A | M36 | | | | | | | 0.05 | 0.04 | 0.00 | | | |
| 37 | A | M37 | | | | | | | 0.62 | 0.21 | 59.53 | | | |
| 38 | A | M38 | | | | | | | 0.78 | 0.75 | 0.00 | | | |
| 39 | A | M39 | | | | | | | 0.70 | 0.40 | 0.00 | | | |
| 40 | A | M40 | | | | | | | 0.49 | 0.24 | 0.00 | | | |
| 41 | A | M41 | | | | | | | 0.73 | 0.16 | 0.00 | | | |
| 42 | A | M42 | | | | | | | 0.48 | 0.23 | 0.00 | | | |
| 43 | B | M1 | 0.82 | | 0.01 | | 2.59 | 0.19 | 0.89 | 0.20 | 0.00 | 1.01 | 0.65 | 0.00 |
| 44 | B | M3 | 0.74 | | 0.01 | 0.81 | | 0.31 | 0.88 | 0.08 | 0.00 | 1.02 | 0.93 | 0.00 |
| 45 | B | M6 | 0.51 | | 0.08 | 0.74 | | 0.32 | 0.73 | 0.06 | 0.00 | 1.02 | 2.10 | 0.00 |
| 46 | B | M8 | | | | | | | 0.89 | 0.19 | 0.00 | | | |
| 47 | B | M10 | 0.66 | | 0.06 | 0.87 | | 0.20 | 0.84 | 0.07 | 0.00 | 1.01 | 1.25 | 0.00 |
| 48 | B | M12 | 0.44 | | 0.09 | 0.94 | | 0.39 | 0.74 | 0.08 | 0.00 | 1.02 | 258 | 0.00 |
| 49 | B | M13 | 0.79 | | 0.02 | 0.77 | | 0.06 | 0.91 | 0.16 | 0.00 | 0.99 | 0.83 | 0.00 |
| 50 | B | M15 | 0.78 | | 0.03 | 0.87 | | 0.08 | 0.89 | 0.09 | 0.00 | 1.01 | 0.76 | 0.00 |
| 51 | B | M17 | 0.58 | | 0.07 | 0.60 | | 0.24 | 0.77 | 0.04 | 0.00 | 1.02 | 1.83 | 0.00 |
| 52 | C | M25 | | | | | | | 0.01 | 0.02 | 0.00 | | | |
| 53 | C | M26 | | | | | | | 0.33 | 0.12 | 0.00 | | | |
| 54 | C | M27 | | | | | | | 0.54 | 0.28 | 0.00 | | | |
| 55 | C | M28 | | | | | | | 0.52 | 0.35 | 0.00 | | | |
| 56 | C | M29 | | | | | | | 0.68 | 0.12 | 0.00 | | | |

TABLE 2-continued

Formula Constants & All Analysis Results

| Example Number | Mixed Metal Compounds | Method of depletion | Formula Constants $[M^{II}_{(1-a)}M^{III}_{(a)}O_b(OH)_dA^{n-}_c \cdot zH_2O]$ a (=$M^{III}$/$M^{III}$+$M^{II}$) | b | c | d | Z | cn/a | Phosphate bound Standard method (1a) mmol/g | Mg release mmol/g | Fe release μmol/g | Phosphate bound Representative method (1b) mmol/g | Mg release mmol/g | Fe release μmol/g |
|---|---|---|---|---|---|---|---|---|---|---|---|---|---|---|
| 57 | D | M25 | 0.84 | 2.35 | 0.02 | 0.45 | 3.09 | 0.05 | 0.76 | 0.20 | 0.00 | | | |
| 58 | D | M26 | 0.77 | 1.65 | 0.02 | 1.08 | 2.88 | 0.04 | 0.73 | 0.15 | 0.08 | | | |
| 59 | D | M27 | 0.63 | 0.95 | 0.03 | 1.62 | 3.32 | 0.09 | 0.73 | | 0.00 | | | |
| 60 | D | M28 | 0.40 | 0.41 | 0.04 | 1.91 | 2.27 | 0.18 | 0.65 | 0.17 | 0.00 | | | |
| 61 | D | M29 | 0.28 | 0.22 | 0.04 | 1.97 | 2.16 | 0.31 | 0.63 | 0.19 | 0.00 | | | |
| 62 | E | M1 | 0.86 | | 0.02 | | 2.84 | 0.05 | 0.46 | 0.24 | 0.00 | | | |
| 63 | E | M2 | 0.85 | | 0.01 | | 3.30 | 0.03 | 0.53 | 0.21 | 0.00 | | | |
| 64 | E | M3 | 0.77 | | 0.02 | | 1.75 | 0.05 | 0.69 | 0.22 | 0.00 | | | |
| 65 | E | M4 | | | | | | | 0.60 | 0.78 | 0.00 | | | |
| 66 | E | M5 | 0.63 | | 0.02 | | 3.44 | 0.05 | 0.66 | 0.95 | 0.00 | | | |
| 67 | E | M6 | | | | | | | 0.26 | 0.57 | 0.38 | | | |
| 68 | E | M7 | | | | | | | | 2.10 | 3.46 | | | |
| 69 | F | M2 | | | | | | | | | | | | |
| 70 | F | M4 | 0.25 | | 0.00 | | 2.90 | 0.02 | 0.94 | 0.20 | 0.00 | 0.26 | 4.04 | 0.00 |
| 71 | F | M6 | 0.22 | | 0.01 | | 2.17 | 0.06 | 0.63 | 0.06 | 0.00 | 0.55 | 2.39 | 0.00 |
| 72 | F | M21 | 0.24 | | 0.01 | | 3.16 | 0.03 | 0.33 | 0.08 | 0.00 | 0.91 | 1.11 | 0.00 |
| 73 | F | M33 | 0.24 | | 0.00 | | 3.70 | 0.01 | 0.82 | 0.40 | 0.00 | 0.14 | 3.72 | 0.00 |
| 74 | F | M35 | 0.25 | | 0.01 | | 2.66 | 0.03 | 0.73 | 0.12 | 0.00 | 0.56 | 2.54 | 0.00 |
| 75 | G | M2 | | | | | | | | | | | | |
| 76 | G | M4 | | | | | | | | | | | | |
| 77 | Q | M2 | | | | | | | 0.09 | 0.00 | 0.00 | | | |
| 78 | Q | M4 | | | | | | | | | | | | |
| 79 | R | M2 | | | | | | | 0.96 | 0.01 | 0.00 | | | |
| 80 | R | M4 | | | | | | | | | | | | |
| 81 | A | M43 | 0.99 | 2.97 | 0.01 | 0.00 | 2.20 | 0.02 | 0.94 | 0.06 | 0.00 | 0.96 | 0.08 | 0.00 |
| 82 | A | M44 | 0.82 | 1.70 | 0.02 | 1.08 | 0.80 | 0.06 | 0.75 | 0.04 | 0.00 | 0.91 | 0.09 | 0.00 |
| 83 | A | M45 | 0.39 | 0.40 | 0.04 | 1.91 | 1.62 | 0.21 | 0.62 | 0.06 | 0.00 | 0.99 | 1.50 | 0.00 |
| 84 | A | M46 | 0.98 | 1.89 | 0.00 | 1.08 | 7.16 | 0.01 | 0.50 | 0.12 | 0.00 | 0.99 | 6.00 | 0.03 |
| 85 | A | M47 | 0.98 | 1.88 | 0.01 | 1.08 | 2.31 | 0.02 | 0.44 | 0.00 | 0.00 | | | |
| 86 | A | M48 | 0.97 | 1.88 | 0.01 | 1.08 | 2.37 | 0.02 | 0.66 | 0.00 | 0.00 | | | |
| 87 | A | M49 | 0.97 | 1.89 | 0.00 | 1.08 | 8.89 | 0.01 | 0.66 | 0.00 | 0.00 | | | |
| 88 | A | M50 | 0.97 | 1.88 | 0.01 | 1.08 | 4.88 | 0.01 | 0.46 | 0.00 | 0.01 | | | |
| 89 | A | M51 | 0.97 | 1.87 | 0.01 | 1.08 | 1.77 | 0.02 | 0.57 | 0.00 | 0.00 | | | |
| 90 | A | M52 | 0.97 | 1.87 | 0.01 | 1.08 | 0.77 | 0.02 | 0.58 | 0.00 | 0.00 | | | |
| 91 | A | M53 | 0.97 | 1.88 | 0.01 | 1.08 | 0.62 | 0.01 | 0.66 | 0.00 | 0.00 | | | |
| 92 | A | M54 | 0.97 | 1.88 | 0.01 | 1.08 | 0.63 | 0.01 | 0.62 | 0.00 | 0.00 | | | |
| 93 | A | M55 | 0.99 | 2.97 | 0.01 | 0.00 | 2.20 | 0.02 | 0.62 | 0.00 | 0.00 | | | |
| 94 | A | M56 | 0.96 | 1.86 | 0.01 | 1.08 | 4.15 | 0.01 | 0.84 | 0.00 | 0.00 | 0.97 | 0.16 | 0.00 |
| 95 | A | M57 | 0.97 | 1.88 | 0.01 | 1.08 | 1.27 | 0.01 | 0.79 | 0.04 | 0.00 | 0.97 | 0.14 | 0.00 |

The phosphate binding capacity, Mg release and Fe release for the different methods of depletion can be seen in FIG. 2.

The magnesium release of a given compound and its phosphate binding capacity will vary according to a number of parameters.

The effect of the constant "a" (wherein "a" is variable a of the general formulae recited herein) on phosphate binding and magnesium release is shown in Table 3.

TABLE 3

Effect of formula constant "a" on phosphate binding and magnesium release

| | | | | Standard Method (1a) | | Representative Method (1b) | |
|---|---|---|---|---|---|---|---|
| | | Time of treatment is: 30 minutes with 1 M HCl | | | Mg | | Mg |
| Example Number | Preparation pH | Structure measured by XRD | a (=$M^{III}/M^{III}+M^{II}$) | P bound mmol/g | release mmol/g | P bound mmol/g | release mmol/g |
| 1 | 3 | non-crystalline | 0.98 | 0.65 | 0.58 | 0.250 | 0.08 |
| 2 | 4 | non-crystalline | 0.92 | 0.84 | 0.17 | 0.86 | 0.25 |
| 3 | 5 | non-crystalline | 0.84 | 0.810 | 0.19 | 0.90 | 1.19 |
| 4 | 6 | Hydrotalcite | 0.58 | 0.86 | 0.29 | 1.02 | 2.45 |
| 5 | 7 | Hydrotalcite | 0.46 | 0.75 | 0.19 | 1.02 | 4.00 |
| 6 | 8 | Hydrotalcite | 0.38 | 0.64 | 0.15 | | |

TABLE 3-continued

Effect of formula constant "a" on phosphate binding and magnesium release

| | | | | Standard Method (1a) | | Representative Method (1b) | |
|---|---|---|---|---|---|---|---|
| | Time of treatment is: 30 minutes with 1 M HCl | | | | Mg | | Mg |
| Example Number | Preparation pH | Structure measured by XRD | a (=$M^{III}/M^{III} + M^{II}$) | P bound mmol/g | release mmol/g | P bound mmol/g | release mmol/g |
| 7 | 9 | Hydrotalcite | 0.34 | 0.60 | 0.16 | | |
| H | FeOOH | | 1.00 | 0.24 | 0.00 | 0.82 | 0.05 |
| A | untreated | Hydrotalcite | 0.34 | 0.71 | 0.17 | 0.99 | 4.66 |

These results are also represented graphically in FIGS. 1 and 2. Thus, it can be seen that increasing the value for the constant "a" up to value 0.98, results in reduced magnesium loss and good phosphate binding.

The effect of treatment time and preparation pH with 1M HCL on compounds of formula (II) is shown in Table 4.

TABLE 4

Effect of treatment time and preparation pH with 1M HCl on compounds of formula (II)

| | | | | XRF (PW2400 Wavelength Dispersive XRF Spectrometer) | | Standard Method |
|---|---|---|---|---|---|---|
| Example Number | Treatment Time minutes | Preparation pH | Yield % | MgO content % | Fe2O3 content % | P bound Analysis-mmol/g |
| 8 | 15 | 3 | 57 | 2.98 | 69.51 | 0.9 |
| 1 | 30 | 3 | 57 | 3.13 | 55.43 | 0.65 |
| 13 | 60 | 3 | 37 | | | |
| 9 | 15 | 4 | 49 | | | 0.77 |
| 2 | 30 | 4 | 43 | 3.98 | 61.24 | 0.84 |
| 14 | 60 | 4 | 43 | | | 0.69 |
| 10 | 15 | 5 | 36 | | | 0.73 |
| 3 | 30 | 5 | 34 | 5.72 | 60.17 | 0.81 |
| 15 | 60 | 5 | | | | 0.69 |
| 11 | 15 | 6 | 72 | 22.54 | 42.09 | 0.74 |
| 4 | 30 | 6 | 63 | 18.74 | 43.28 | 0.86 |
| 16 | 60 | 6 | 51 | 14.18 | 55.09 | 0.76 |
| 12 | 15 | 8 | 90 | | | 0.6 |
| 6 | 30 | 8 | 90 | 26 | 32.13 | 0.64 |
| 17 | 60 | 8 | 81 | | | 0.59 |
| A | no treatment | | | 28.46 | 30.22 | 0.71 |

Yield for Depleted Product (%) = (weight of depleted product (g)/weight of initial material (g)) × 100

As can be seen from the results in Table 4, there is an optimal time period of treatment whereby the magnesium can be removed from the compound whilst maintaining the iron within the structure. A treatment time of 30 minutes, using a preparation pH of 4 results in an MgO content of 3.98% and a 0.93 mmol/g bound phosphate. The yield for this sample was 43%.

A period of treatment which is less than 15 minutes will result in less magnesium being depleted from the compound than is desirable, resulting in small improvements in phosphate binding.

Moreover, prolonged periods of treatment of 60 minutes or longer results in the Mg-depleted compound itself being degraded resulting in a loss of yield in addition to a loss in phosphate binding.

Further, extremes of low pH and long periods of treatment tend to result in removal of the iron from the compound structure.

Thus, the data in Table 4 shows that the optimum treatment time within the pH range of 4 to 8 is 30 minutes. The optimum treatment time at pH 3 is 15 minutes.

However, it will be clear to the person skilled in the art that the optimum treatment time will vary depending on the conditions of treatment used e.g. variations in amount of starting material, acid type, concentration, treatment pH etc.

TABLE 5

Compositions and structure as measured by XRF and XRD

| | | | | Composition | | | | | | |
|---|---|---|---|---|---|---|---|---|---|---|
| Example Number | Mixed Metal Compounds | Method of depletion | Yield % | $M^{3+}_2O_3$ % wt. Measured by XRF | $Mg^{2+}O$ % wt. Measured by XRF | CO2 % wt Measured by Leco. | H2O % wt. Measured by calculation | Na2O % wt Measured by XRF | SO3 % wt Measured by XRF | Structure measured by XRD |
| Starting materials | | | | | | | | | | |
| A | Mg2Fe | M0 | | 30.22 | 28.46 | 6.48 | 32.26 | 0.15 | 2.43 | Hydrotalcite |
| B | Mg2Fe calcined | M0 | | 46.63 | 44.94 | 0.52 | 3.59 | 0.30 | 4.02 | non-crystalline |

TABLE 5-continued

Compositions and structure as measured by XRF and XRD

| Example Number | Mixed Metal Compounds | Method of depletion | Yield % | $M^{3+}_2O_3$ % wt. Measured by XRF | $Mg^{2+}O$ % wt. Measured by XRF | $CO_2$ % wt Measured by Leco. | $H_2O$ % wt. Measured by calculation | $Na_2O$ % wt Measured by XRF | $SO_3$ % wt Measured by XRF | Structure measured by XRD |
|---|---|---|---|---|---|---|---|---|---|---|
| C | Mg2Fe slurry | M0 | | | | | | | | |
| D | Mg2Fe wet cake | M0 | | 39.77 | 12.17 | 1.65 | 44.13 | 0.55 | 1.73 | Hydrotalcite |
| E | Mg4Fe | M0 | | 18.00 | 35.52 | 2.23 | 37.58 | 1.61 | 5.06 | Hydrotalcite |
| F | $Mg_3Al$ | M0 | | 24.86 | 15.00 | 1.91 | 57.96 | 0.00 | 2.85 | Hydrotalcite |
| G | $Mg^{II}Fe^{II}Fe^{III}$ | M0 | | 16.03 | 4.86 | 1.37 | 28.50 | 30.34 | 18.90 | non-crystalline |
| H | FeOOH (Sigma) | M0 | | | | | | | | |
| I | Fe2O3 (Sigma) | M0 | | | | | | | | |
| J | FeOOH/MgOH mix | M0 | | 59.28 | 31.80 | 0.00 | 8.88 | 0.00 | 0.04 | |
| K | FeOOH/MgOH mix | M0 | | 72.70 | 16.86 | 0.00 | 10.37 | 0.02 | 0.05 | |
| L | Fe2O3/MgO mix | M0 | | 67.38 | 33.38 | 0.00 | 0.00 | 0.00 | 0.06 | |
| M | Fe2O3/MgO mix | M0 | | 83.10 | 18.14 | 0.00 | 0.00 | 0.00 | 0.06 | |
| N | MgFe pH5 prec. | M0 | | 76.87 | 0.06 | 0.05 | 18.07 | 0.00 | 5.34 | |
| O | MgFe pH10 prec. | M0 | | 42.36 | 19.77 | 1.60 | 35.28 | 0.00 | 0.99 | |
| P | FeOOH (prec) | M0 | | 72.31 | 0.02 | 1.74 | 20.59 | 0.00 | 5.34 | |
| Q | Lanthanum carbonate | M0 | | | | | | | | |
| R | sevelamer | M0 | | | | | | | | |
| | Mg-depleted materials | | | | | | | | | |
| 1 | A | M1 | 57 | 55.43 | 3.13 | 0.08 | 36.69 | 0.00 | 4.67 | non-crystalline |
| 2 | A | M2 | 43 | 61.24 | 3.98 | 0.19 | 31.94 | 0.03 | 2.62 | non-crystalline |
| 3 | A | M3 | 34 | 60.17 | 5.72 | 0.19 | 32.35 | 0.02 | 1.55 | non-crystalline |
| 4 | A | M4 | 63 | 43.28 | 18.74 | 5.40 | 30.95 | 0.00 | 1.63 | Hydrotalcite |
| 5 | A | M5 | 79 | 36.01 | 24.44 | 1.52 | 36.34 | 0.00 | 1.69 | Hydrotalcite |
| 6 | A | M6 | 90 | 32.13 | 26.00 | | | | | Hydrotalcite |
| 7 | A | M7 | 94 | 31.34 | 28.04 | | | | | Hydrotalcite |
| 8 | A | M8 | 57 | 69.51 | 2.98 | | | | | |
| 9 | A | M9 | 49 | | | | | | | |
| 10 | A | M10 | 36 | | | | | | | |
| 11 | A | M11 | 72 | 42.09 | 22.54 | 5.45 | 28.34 | 0.00 | 1.58 | |
| 12 | A | M12 | 90 | | | | | | | |
| 13 | A | M13 | 37 | | | | | | | |
| 14 | A | M14 | 43 | | | | | | | |
| 15 | A | M15 | 90 | | | | | | | |
| 16 | A | M16 | 51 | 55.09 | 14.18 | 3.97 | 25.10 | 0.00 | 1.66 | |
| 17 | A | M17 | 81 | | | | | | | |
| 18 | A | M18 | 51 | 51.46 | 0.61 | | | | | non-crystalline |
| 19 | A | M19 | 53 | 49.07 | 2.03 | | | | | non-crystalline |
| 20 | A | M20 | 58 | 46.81 | 7.68 | | | | | non-crystalline |
| 21 | A | M21 | 81 | 32.27 | 19.29 | | | | | Hydrotalcite |
| 22 | A | M22 | 99 | 29.15 | 27.16 | 1.39 | 41.01 | 0.30 | 0.99 | Hydrotalcite |
| 23 | A | M23 | 96 | 28.23 | 26.91 | 1.50 | 42.33 | 0.29 | 0.74 | Hydrotalcite |
| 24 | A | M24 | 96 | 29.12 | 27.94 | 1.55 | 40.26 | 0.32 | 0.81 | Hydrotalcite |
| 25 | A | M25 | 48 | | | | | | | |
| 26 | A | M26 | 49 | | | | | | | |
| 27 | A | M27 | 58 | | | | | | | |
| 28 | A | M28 | 77 | | | | | | | |
| 29 | A | M29 | 86 | | | | | | | |
| 30 | A | M30 | | | | | | | | |
| 31 | A | M31 | | | | | | | | |
| 32 | A | M32 | | | | | | | | |
| 33 | A | M33 | 42 | | | | | | | |
| 34 | A | M34 | 79 | | | | | | | |
| 35 | A | M35 | 90 | | | | | | | |
| 36 | A | M36 | 3 | | | | | | | |
| 37 | A | M37 | 30 | | | | | | | |
| 38 | A | M38 | 44 | | | | | | | |
| 39 | A | M39 | 55 | | | | | | | |
| 40 | A | M40 | 89 | | | | | | | |
| 41 | A | M41 | | | | | | | | |
| 42 | A | M42 | | | | | | | | |
| 43 | B | M1 | 55 | 49.37 | 5.60 | 0.03 | 41.96 | 0.01 | 3.03 | |
| 44 | B | M3 | 60 | 65.42 | 10.95 | 0.16 | 21.30 | 0.05 | 2.12 | |
| 45 | B | M6 | 78 | 54.57 | 19.31 | 3.51 | 21.15 | 0.00 | 1.46 | |
| 46 | B | M8 | 55 | | | | | | | |
| 47 | B | M10 | 64 | 46.36 | 10.68 | 2.70 | 38.94 | 0.03 | 1.29 | |
| 48 | B | M12 | 82 | 54.40 | 23.40 | 3.70 | 18.31 | 0.11 | 0.08 | |
| 49 | B | M13 | 57 | 56.53 | 9.16 | 0.44 | 30.20 | 0.02 | 3.65 | |
| 50 | B | M15 | 58 | 59.40 | 8.35 | 1.01 | 28.87 | 0.01 | 2.36 | |
| 51 | B | M17 | 72 | 49.89 | 15.61 | 2.97 | 30.25 | 0.02 | 1.26 | |
| 52 | C | M25 | | | | | | | | |
| 53 | C | M26 | | | | | | | | |

TABLE 5-continued

Compositions and structure as measured by XRF and XRD

| Example Number | Mixed Metal Compounds | Method of depletion | Yield % | Composition $M^{3+}_2O_3$ % wt. Measured by XRF | $Mg^{2+}O$ % wt. Measured by XRF | $CO_2$ % wt Measured by Leco. | $H_2O$ % wt. Measured by calculation | $Na_2O$ % wt Measured by XRF | $SO_3$ % wt Measured by XRF | Structure measured by XRD |
|---|---|---|---|---|---|---|---|---|---|---|
| 54 | C | M27 | | | | | | | | |
| 55 | C | M28 | | | | | | | | |
| 56 | C | M29 | | | | | | | | |
| 57 | D | M25 | | 47.02 | 4.37 | 0.18 | 38.86 | 0.04 | 9.53 | |
| 58 | D | M26 | | 46.67 | 7.15 | 0.25 | 39.52 | 0.11 | 6.30 | |
| 59 | D | M27 | | 38.29 | 11.55 | 0.96 | 45.79 | 0.05 | 3.36 | |
| 60 | D | M28 | | 31.77 | 24.23 | 1.53 | 40.84 | 0.04 | 1.59 | |
| 61 | D | M29 | | 23.53 | 31.13 | 1.80 | 41.43 | 0.04 | 2.07 | |
| 62 | E | M1 | | 49.24 | 4.21 | 0.04 | 36.82 | 0.17 | 9.52 | |
| 63 | E | M2 | | 47.36 | 4.38 | 0.06 | 41.75 | 0.19 | 6.26 | |
| 64 | E | M3 | | 57.03 | 8.77 | 0.44 | 29.35 | 0.36 | 4.05 | |
| 65 | E | M4 | | | | | | | | |
| 66 | E | M5 | | 38.43 | 11.57 | 0.64 | 47.56 | 0.23 | 1.57 | |
| 67 | E | M6 | | | | | | | | |
| 68 | E | M7 | | | | | | | | |
| 69 | F | M2 | | | | | | | | |
| 70 | F | M4 | | 31.06 | 18.36 | 0.87 | 43.24 | 2.71 | 3.76 | |
| 71 | F | M6 | | 30.42 | 21.34 | 1.73 | 33.84 | 2.47 | 10.20 | |
| 72 | F | M21 | | 28.58 | 18.05 | 0.87 | 44.97 | 2.42 | 5.11 | |
| 73 | F | M33 | | 26.80 | 16.91 | 6.45 | 43.93 | 3.76 | 2.15 | |
| 74 | F | M35 | | 31.24 | 18.74 | 2.92 | 38.05 | 2.92 | 6.13 | |
| 75 | G | M2 | | | | | | | | |
| 76 | G | M4 | | | | | | | | |
| 77 | Q | M2 | | | | | | | | |
| 78 | Q | M4 | | | | | | | | |
| 79 | R | M2 | | | | | | | | |
| 80 | R | M4 | | | | | | | | |
| 81 | A | M43 | 24 | 64.32 | 0.48 | 0.06 | 32.36 | 0.00 | 2.78 | non-crystalline |
| 82 | A | M44 | 36 | 81.28 | 0.72 | 0.13 | 15.46 | 0.00 | 2.41 | non-crystalline |
| 83 | A | M45 | 45 | 74.34 | 7.98 | 0.95 | 16.26 | 0.00 | 0.47 | non-crystalline |
| 84 | A | M46 | 82 | 35.68 | 27.96 | 1.77 | 33.27 | 0.00 | 1.32 | Hydrotalcite |
| 85 | A | M47 | 60 | 37.26 | 0.44 | 0.15 | 61.61 | 0.00 | 0.54 | non-crystalline |
| 86 | A | M48 | 60 | 63.94 | 0.8 | 0.26 | 34.08 | 0.00 | 0.92 | non-crystalline |
| 87 | A | M49 | 60 | 63.3 | 0.84 | 0.26 | 34.69 | 0.00 | 0.91 | non-crystalline |
| 88 | A | M50 | 66 | 32.4 | 0.44 | 0.17 | 66.73 | 0.00 | 0.26 | non-crystalline |
| 89 | A | M51 | 66 | 46.38 | 0.62 | 0.24 | 52.43 | 0.00 | 0.33 | non-crystalline |
| 90 | A | M52 | 66 | 69.64 | 0.94 | 0.37 | 28.58 | 0.00 | 0.47 | non-crystalline |
| 91 | A | M53 | 33 | 82.78 | 1.26 | 0.23 | 14.80 | 0.00 | 0.93 | non-crystalline |
| 92 | A | M54 | 33 | 85.18 | 1.34 | 0.18 | 12.35 | 0.00 | 0.95 | non-crystalline |
| 93 | A | M55 | 33 | 85.08 | 1.32 | 0.15 | 12.49 | 0.00 | 0.96 | non-crystalline |
| 94 | A | M56 | 67 | 49.62 | 1.08 | 0.25 | 48.45 | 0.00 | 0.60 | |
| 95 | A | M57 | 39 | 75.02 | 1.02 | 0.03 | 22.13 | 0.03 | 1.77 | |

It can be seen from the results of Table 5 that methods of depletion utilising a low preparation pH (3-5) tend to produce compounds having a non-crystalline structure. Methods of depletion utilising a preparation pH of above 5 tend to produce compounds having a hydrotalcite structure. The results of Table 5 are also represented graphically in FIG. 5.

TABLE 6

Effect of washing

| Example Number | Volume of Wash Water ml | Preparation pH | XRF (PW2400 Wavelength Dispersive XRF Spectrometer) MgO content % | $Fe_2O_3$ content % | Standard Method (1a) P bound Analysis — mmol/g | Mg Release Mmol/g | Representative Method (1b) P bound Analysis — mmol/g | Mg Release mmol/g |
|---|---|---|---|---|---|---|---|---|
| 1 | 600 | 3 | 3.13 | 55.43 | 0.65 | 0.58 | 0.25 | 0.08 |
| 43 | 3000 | 3 | 0.48 | 64.32 | 0.94 | 0.06 | 0.96 | 0.08 |
| 2 | 600 | 4 | 3.98 | 61.24 | 0.84 | 0.17 | 0.86 | 0.25 |
| 44 | 3000 | 4 | 0.72 | 81.28 | 0.75 | 0.04 | 0.91 | 0.09 |
| 3 | 600 | 5 | 5.72 | 60.17 | 0.81 | 0.19 | 0.90 | 1.19 |

TABLE 6-continued

Effect of washing

| Example Number | Volume of Wash Water ml | Preparation pH | XRF (PW2400 Wavelength Dispersive XRF Spectrometer) MgO content % | Fe2O3 content % | Standard Method (1a) P bound Analysis mmol/g | Mg Release Mmol/g | Representative Method (1b) P bound Analysis mmol/g | Mg Release mmol/g |
|---|---|---|---|---|---|---|---|---|
| 45 | 3000 | 5 | 7.98 | 74.34 | 0.62 | 0.06 | 0.99 | 1.50 |
| 5 | 600 | 7 | 24.44 | 36.01 | 0.75 | 0.19 | 1.02 | 4.00 |
| 46 | 3000 | 7 | 27.96 | 35.68 | 0.50 | 0.12 | 0.99 | 6.00 |

The effect of increasing the volume of wash water on the composition of the depleted material is most evident at a lower preparation pH. The MgO content indicates that the product contains a significant percentage of magnesium salts, produced during depletion. The 3 L wash produces a significantly more pure depleted product. The representative method indicates that phosphate binding capacity increases with higher volumes of wash water. The effect of increased washing is especially demonstrated by the results obtained via the standard method.

TABLE 7

Effect of acid addition method

| Example Number | Acid Addition Method | XRF (PW2400 Wavelength Dispersive XRF Spectrometer) MgO content % | Fe2O3 content % | Standard Method (1a) P bound Analysis mmol/g | Mg Release mmol/g | Representative Method (1b) P bound Analysis mmol/g | Mg Release mmol/g |
|---|---|---|---|---|---|---|---|
| 94 | Total (I) | 1.08 | 49.62 | 0.84 | 0.00 | 0.97 | 0.16 |
| 95 | Slow (II) | 1.02 | 75.02 | 0.79 | 0.04 | 0.97 | 0.14 |

(I) Total Acid Addition 825 ml 1M HCl at 0 minutes
(II) Slow Acid Addition, rate 10 ml/min for first 40 minutes then 5 ml/min for additional 20 mins then 2.5 ml/min for remaining 10 minutes, total addition time 70 mins The data indicates the slow acid addition affects the constitution of the depleted material. The iron oxide content increases by approximately 25% w/w. This also shows that the total acid addition method produces impurity products due to extremely low pH conditions achieved by the sudden addition of a large amount of acid. As a result the phosphate binding capacity is reduced and magnesium release increases in the Representative Method.

TABLE 8

Effect of drying method

| Example Number | Drying Time Hrs | Drying Temperature ° C. | XRF (PW2400 Wavelength Dispersive XRF Spectrometer) MgO content % | Fe2O3 content % | Standard Method P bound Analysis mmol/g | Mg Release mmol/g |
|---|---|---|---|---|---|---|
| 85 | 1.5 | 40 | 0.44 | 37.26 | 0.44 | 0.00 |
| 88 | 1.5 | 80 | 0.44 | 32.4 | 0.46 | 0.00 |
| 91 | 1.5 | 120 | 1.26 | 82.78 | 0.66 | 0.00 |
| 86 | 3 | 40 | 0.8 | 63.94 | 0.66 | 0.00 |
| 89 | 3 | 80 | 0.62 | 46.38 | 0.57 | 0.00 |
| 92 | 3 | 120 | 1.34 | 85.18 | 0.62 | 0.00 |
| 87 | 4 | 40 | 0.84 | 63.3 | 0.66 | 0.00 |
| 90 | 4 | 80 | 0.94 | 69.64 | 0.58 | 0.00 |
| 93 | 4 | 120 | 1.32 | 85.08 | 0.62 | 0.00 |

The data indicates that the optimum drying temperature is 40° C. for 3 hrs, these conditions produce to best phosphate binding and magnesium release. High drying temperatures for the same time period produce compounds with higher MgO content when compared to the same material dried at lower temperature.

release between examples A and 2 and between examples A and 5 (p<0.0001 for both), but there was not a statistical difference between examples 2 and 5 (p<0.5, NS).

TABLE 9

Determination of the phosphate binding capacity at different concentration

| Example Number | a (=M$^{III}$/ M$^{III}$ + M$^{II}$) | Standard Method 1a | | | Representative Method 1b (0.4 g dose) | | | Representative Method 1c (0.2 g dose) | | |
|---|---|---|---|---|---|---|---|---|---|---|
| | | P bound Analysis mmol/g | Mg Release mmol/g | Ratio P bound:Mg release | P bound Analysis mmol/g | Mg Release mmol/g | Ratio P bound:Mg release | P bound Analysis mmol/g | Mg Release mmol/g | Ratio P bound:Mg release |
| 1 | 0.98 | 0.65 | 0.58 | 1.12 | 0.25 | 0.08 | 3.13 | 1.02 | 0.73 | 1.40 |
| 2 | 0.92 | 0.84 | 0.17 | 4.94 | 0.86 | 0.25 | 3.44 | 0.95 | 0.23 | 4.13 |
| 3 | 0.84 | 0.81 | 0.19 | 4.26 | 0.90 | 1.19 | 0.76 | 1.17 | 0.83 | 1.41 |
| 4 | 0.58 | 0.86 | 0.29 | 2.96 | 1.02 | 2.45 | 0.42 | 1.97 | 3.76 | 0.52 |
| 5 | 0.46 | 0.75 | 0.19 | 3.95 | 1.02 | 4.00 | 0.26 | 1.98 | 5.59 | 0.35 |
| 6 | 0.38 | 0.64 | 0.15 | 4.27 | | | | 1.98 | 6.46 | 0.31 |
| 7 | 0.34 | 0.60 | 0.16 | 3.75 | | | | | | |
| A | 0.34 | 0.71 | 0.17 | 4.18 | 0.99 | 6.18 | 0.16 | 1.99 | 6.58 | 0.30 |
| H | 1.00 | 0.24 | 0.00 | — | 0.81 | 0.05 | 16.2 | 0.85 | 0.05 | 17.0 |

The desired 'a' value range for the Standard Method (0.60-0.99), Representative Method 0.4 g (0.70-0.99), Representative Method 0.2 g (0.80-0.99). The Standard Pi Binding Method gives lower Magnesium release values because the pH of the solution is not maintained and therefore rises from the initial pH of 4 to approximately pH 9 depending on the depletion conditions used. At high pH conditions the Mg Release is reduced.

FIG. 1 shows "a" as function of phosphate bound measured by 2 binding methods.

The standard method (Test Method 1a) is a standard phosphate binding method

The representative method (Test Method 1b) is a method chosen to more closely mimic the conditions of the stomach Both methods showed increased or maintained phosphate binding as function of "a" up to 0.95.

TABLE 10

Pi binding and magnesium release determined in GI tract model

| Example Number | a (=M$^{III}$/M$^{III}$ + M$^{II}$) | P bound Analysis mmol/g | Mg Release mmol/g | Ratio P bound:Mg release | P bound Bonferroni multiple comparison test p value | Mg release Bonferroni multiple comparison test p value |
|---|---|---|---|---|---|---|
| A | 0.34 | 136 | 33 | 4.12 | — | — |
| 2 | 0.98 | 83 | 9.0 | 9.22 | A v 2, NS | A v 2, 0.0001 |
| 5 | 0.39 | 92 | 23 | 4.00 | A v 5, NS 2 v 5, NS | A v 5, 0.0001 2 v 5, NS |

* Values are the mean of 4 experiments,
NS = not significant

An overall increase in phosphate binding was observed using this more appropriate gastric test model. From this table it can be concluded that a higher degree of variation in phosphate binding and magnesium release exists in the GI tract model than by the standard or representative method 1a or 1b. Depletion at low pH (providing a=0.98 compound), magnesium release was significantly less and phosphate binding capacity was maintained, while depletion at higher pH (providing a=0.39 compound) a similar phosphate binding capacity was evident but with a greater magnesium release. Other variations were not tested but this provides proof of principle that depletion of Mg results in low release of magnesium while maintaining phosphate binding capacity. Using a Bonferroni multiple comparison test (columns 5 and 6) there was no statistical difference in phosphate binding capacity between examples A, 2 or 5 (p<0.05, NS). However, there was a statistical difference in magnesium Both methods show decreased phosphate binding between "a"=0.95 and 1.0 which can be explained by dissolution of the compound upon exposure to extreme low acidic pH and time.

FIG. 2 shows "a" as function of magnesium released (from the phosphate binder). It is preferred to have less release of magnesium.

The standard method (Test Method 1a) is a standard magnesium release analysis method (measured at the same time and equipment/method as with standard phosphate binding)

The representative method (Test Method 1b) is a method chosen to more closely mimic the conditions of the stomach The standard method shows a relatively constant level of magnesium release because in this test method the pH is allowed to rise from pH 4 to 9 at which magnesium release is less significant.

The representative method shows Mg release decreasing as "a" increases. With this test method pH is maintained constant (at pH 3) resulting in more acid attack on the structure. Consequently, with this test there is a higher propensity to release magnesium, when un-depleted, than in the standard test method.

Conclusion from FIGS. 1 and 2 Combined

When combining the data of FIGS. 1 and 2 it was surprising to find that the removal of magnesium from the mixed metal compound resulted in a new magnesium-depleted mixed metal compound indicated by increase of value for "a" above 0.35 which did not show a reduction of the binding of phosphate whilst simultaneously decreasing the potential for release of magnesium during the phosphate-binding process, in particular under more gastric (stomach) conditions of the representative method 1b.

The untreated material typically has value of "a"=0.35.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

The invention claimed is:

1. A pharmaceutical composition comprising
 (a) a phosphate binding mixed metal compound according to formula (I)

$$[M^{II}_{1-a}M^{III}_{a}] \quad (I)$$

wherein $M^{II}$ is at least one bivalent metal, and the at least one bivalent metal comprises Mg(II);
$M^{III}$ is at least one trivalent metal; and
$0.98 > a \geq 0.7$;
the compound contains at least one n-valent anion $A^{n-}$ such that the compound is charge neutral, and the mixed metal compound comprises less than 15% water soluble salts by weight of the mixed metal compound after drying; and
 (b) a pharmaceutically acceptable carrier, diluent, excipient or adjuvant.

2. The pharmaceutical composition of claim 1, wherein the mixed metal compound is of formula (IV)

$$[M^{II}_{1-a}M^{III}_{a}O_{b}(OH)_{d}](A^{n-})_{c} \cdot zH_{2}O \quad (IV)$$

$0 \leq b \leq 2$;
the value of c for each anion is determined by the need for charge neutrality as expressed by the formula $2+a-2b-d-cn=0$; and
$0 \leq d \leq 2$;
$0 \leq z \leq 5$.

3. The pharmaceutical composition of claim 1, wherein at least one anion $A^{n-}$ is carbonate.

4. The pharmaceutical composition of claim 1, wherein $M^{II}$ further comprises a bivalent metal selected from the group consisting of Zn (II), Fe (II), Cu (II), Ca (II), La (II), Ce (II) and Ni(II).

5. The pharmaceutical composition of claim 1, wherein $M^{III}$ is selected from one or more members of the group consisting of Al (III), Mn(III), Fe(III), La(III), and Ce(III).

6. The pharmaceutical composition of claim 1, wherein $M^{III}$ is selected from one or more members of the group consisting of Mn(III), Fe(III), La(III), and Ce(III).

7. The pharmaceutical composition of claim 1, wherein the phosphate binding mixed metal compound is of formula (IV)

$$[M^{II}_{1-a}M^{III}_{a}O_{b}(OH)_{d}](A^{n-})_{c} \cdot zH_{2}O \quad (IV)$$

wherein $M^{II}$ is at least one bivalent metal, and the at least one bivalent metal comprises Mg(II);
$M^{III}$ is at least one trivalent metal selected from the group consisting of Mn(III), Fe(III), La(III), and Ce(III); and
$A^{n-}$ is at least one n-valent anion and wherein at least one anion is carbonate;
$0.98 > a \geq 0.7$;
$0 \leq b \leq 2$;
the value of c for each anion is determined by the need for charge neutrality as expressed by the formula $2+a-2b-d-cn=0$;
$0 \leq d \leq 2$;
$0 < z \leq 5$; and
the mixed metal compound comprises less than 15% water soluble salts by weight of the mixed metal compound after drying.

8. A method of binding phosphate in a subject, comprising administering to a subject a phosphate binding mixed metal compound of formula (I)

$$[M^{II}_{1-a}M^{III}_{a}] \quad (I)$$

wherein $M^{II}$ is at least one bivalent metal, and the at least one bivalent metal comprises Mg(II);
$M^{III}$ is at least one trivalent metal; and
$0.98 > a \geq 0.7$;
the compound contains at least one n-valent anion $A^{n-}$ such that the compound is charge neutral, and the mixed metal compound comprises less than 15% water soluble salts by weight of the mixed metal compound after drying.

9. The method of claim 8, wherein the mixed metal compound is of formula (IV)

$$[M^{II}_{1-a}M^{III}_{a}O_{b}(OH)_{d}](A^{n-})_{c} \cdot zH_{2}O \quad (IV)$$

$0 \leq b \leq 2$;
the value of c for each anion is determined by the need for charge neutrality as expressed by the formula $2+a-2b-d-cn=0$; and
$0 \leq d \leq 2$;
$0 \leq z \leq 5$.

10. The method of claim 8, wherein at least one anion $A^{n-}$ is carbonate.

11. The method of claim 8, wherein $M^{II}$ further comprises a bivalent metal selected from one or more members of the group consisting of Zn (II), Fe (II), Cu (II), Ca (II), La (II), Ce (II), and Ni(II).

12. The method of claim 8, wherein $M^{III}$ is selected from one or more members of the group consisting of Al (III), Mn(III), Fe(III), La(III), and Ce(III).

13. The method of claim 8, wherein $M^{III}$ is selected from one or more members of the group consisting of Mn(III), Fe(III), La(III), and Ce(III).

14. The method of claim 8, wherein the phosphate binding mixed metal compound is of formula (IV)

$$[M^{II}_{1-a}M^{III}_{a}O_{b}(OH)_{d}](A^{n-})_{c} \cdot zH_{2}O \quad (IV)$$

wherein $M^{II}$ is at least one bivalent metal, and the at least one bivalent metal comprises Mg(II);

$M^{III}$ is at least one trivalent metal selected from the group consisting of Mn(III), Fe(III), La(III), and Ce(III); and $A^{n-}$ is at least one n-valent anion and wherein at least one anion is carbonate;

$0.98 > a \geq 0.7$;

$0 \leq b \leq 2$;

the value of c for each anion is determined by the need for charge neutrality as expressed by the formula $2+a-2b-d-cn=0$;

$0 \leq d \leq 2$;

$0 < z \leq 5$; and the mixed metal compound comprises less than 15% water soluble salts by weight of the mixed metal compound after drying.

15. A method for the treatment in a subject of any one of hyperphosphataemia, renal insufficiency, hypoparathyroidism, pseudohypoparathyroidism, acute untreated acromegaly, chronic kidney disease and over medication of phosphate salts, comprising administering to the subject a phosphate binding mixed metal compound of formula (I)

$$M^{II}_{1-a}M^{III}_{a} \qquad (I)$$

wherein $M^{II}$ is at least one bivalent metal, and the at least one bivalent metal comprises Mg(II); $M^{III}$ is at least one trivalent metal; and $0.98 > a \geq 0.7$;

the compound contains at least one n-valent anion $A^{n-}$ such that the compound is charge neutral, and the mixed metal compound comprises less than 15% water soluble salts by weight of the mixed metal compound after drying.

16. The method of claim 15, wherein the mixed metal compound is of formula (IV)

$$[M^{II}_{1-a}M^{III}_{a}O_{b}(OH)_{d}](A^{n-})_{c} \cdot zH_{2}O \qquad (IV)$$

$0 \leq b \leq 2$;

the value of c for each anion is determined by the need for charge neutrality as expressed by the formula $2+a-2b-d-cn=0$; and $0 \leq d \leq 2$;

$0 \leq z \leq 5$.

17. The method of claim 15, wherein at least one anion $A^{n-}$ is carbonate.

18. The method of claim 15, wherein $M^{II}$ further comprises a bivalent metal selected from one or more members of the group consisting of Zn (II), Fe (II), Cu (II), Ca (II), La (II), Ce (II), and Ni(II).

19. The method of claim 15, wherein $M^{III}$ is selected from one or more members of the group consisting of Al (III), Mn(III), Fe(III), La(III), and Ce(III).

20. The method of claim 15, wherein $M^{III}$ is selected from one or more members of the group consisting of Mn(III), Fe(III), La(III), and Ce(III).

21. The method of claim 15, wherein the phosphate binding mixed metal compound is of formula (IV)

$$[M^{II}_{1-a}M^{III}_{a}O_{b}(OH)_{d}](A^{n-})_{c} \cdot zH_{2}O \qquad (IV)$$

wherein $M^{II}$ is at least one bivalent metal, and the at least one bivalent metal comprises Mg(II);

$M^{III}$ is at least one trivalent metal selected from the group consisting of Mn(III), Fe(III), La(III), and Ce(III); and $A^{n-}$ is at least one n-valent anion and wherein at least one anion is carbonate;

$0.98 > a \geq 0.7$;

$0 \leq d \leq 2$;

the value of c for each anion is determined by the need for charge neutrality as expressed by the formula $2+a-2b-d-cn=0$;

$0 \leq d \leq 2$;

$0 < z \leq 5$; and the mixed metal compound comprises less than 15% water soluble salts by weight of the mixed metal compound after drying.

22. The method of claim 15 comprising administering to the patient the mixed metal compound of formula (I) for the treatment of hyperphosphataemia.

23. A phosphate binding mixed metal compound comprising formula (IV)

$$[M^{II}_{1-a}M^{III}_{a}O_{b}(OH)_{d}](A^{n-})_{c} \cdot zH_{2}O \qquad (IV)$$

wherein $M^{II}$ is at least one bivalent metal, and the at least one bivalent metal comprises Mg (II);

$M^{III}$ is at least one trivalent metal selected from the group consisting of Mn(III), Fe(III), La(III), and Ce(III); and $A^{n-}$ is at least one n-valent anion and wherein at least one anion is carbonate;

$0.98 > a \geq 0.7$;

$0 \leq d \leq 2$;

the value of c for each anion is determined by the need for charge neutrality as expressed by the formula $2+a-2b-d-cn=0$;

$0 \leq d \leq 2$;

$0 < z \leq 5$; and the mixed metal compound comprises less than 15% water soluble salts by weight of the mixed metal compound after drying.

24. The mixed metal compound of claim 23, wherein d is 0.

25. The mixed metal compound of claim 23, wherein $0 < d \leq 2$.

26. The mixed metal compound of claim 23, wherein b is 0.

27. The mixed metal compound of claim 23, wherein $0 < b \leq 2$.

28. The mixed metal compound of claim 23, wherein b is 1.5 or less.

29. The mixed metal compound of claim 23, wherein b is 1.2 or less.

30. The mixed metal compound of claim 23, wherein d is 1 or less.

31. The mixed metal compound of claim 23, wherein $0 \leq z \leq 2$.

32. The mixed metal compound of claim 23, wherein $z \leq 1.5$.

33. The mixed metal compound of claim 23, wherein $0.95 > a \geq 0.7$.

34. The mixed metal compound of claim 23, wherein $0.9 > a \geq 0.7$.

35. The mixed metal compound of claim 23, wherein $0.85 > a \geq 0.7$.

36. The mixed metal compound of claim 23, wherein a has the value 0.7.

37. The mixed metal compound of claim 23, wherein $M^{III}$ is at least Fe(III).

38. The mixed metal compound of claim 23, wherein $M^{III}$ is Fe(III).

39. The mixed metal compound of claim 23, wherein $M^{II}$ is at least Mg(II).

40. The mixed metal compound of claim 23, wherein $M^{II}$ is Mg(II).

41. The mixed metal compound of claim 23, wherein $M^{II}$ is Mg(II) and $M^{II}$ is Fe(III).

42. The mixed metal compound of claim 23, wherein $A^{n-}$ is selected from one or more members of the group consisting of carbonate, hydrogencarbonate, sulphate, nitrate, halide, and hydroxide, wherein at least one $A^{n-}$ is carbonate.

43. The mixed metal compound of claim 23, wherein $A^{n-}$ is carbonate.

44. The mixed metal compound of claim 23, obtained by treatment with an acid, a chelating agent or a mixture thereof of a starting material compound according to formula (IV)

$$[M^{II}_{1-a}M^{III}_{a}O_{b}(OH)_{d}](A^{n-})_{c}\cdot zH_{2}O \qquad (IV)$$

wherein $M^{II}$ is at least one bivalent metal, and the at least one bivalent metal comprises Mg (II);
$M^{III}$ is at least one trivalent metal selected from the group consisting of Mn(III), Fe(III), La(III), and Ce(III); and
$A^{n-}$ is at least one n-valent anion and wherein at least one anion is carbonate;
$0<a\leq 0.4$;
$0\leq d\leq 2$;
the value of c for each anion is determined by the need for charge neutrality as expressed by the formula $2+a-2b-d-cn=0$; and
$0\leq d\leq 2$;
$0<0\leq z\leq 5$.

45. The mixed metal compound of claim 44, wherein the compound obtained by the treatment of the starting material compound is further subjected to heat treatment.

46. The mixed metal compound of claim 45, wherein the heat treatment is calcination.

47. The mixed metal compound of claim 44, wherein the acid or chelating agent is hydrochloric acid.

48. The mixed metal compound of claim 44, wherein the acid or chelating agent is hydrochloric acid at a concentration in a range of 2 M to 0.1 M.

49. The mixed metal compound of claim 44, wherein the acid or chelating agent is hydrochloric acid at a concentration in a range of 1.5 to 0.5 M.

50. The mixed metal compound of claim 44, wherein the acid or chelating agent is hydrochloric acid at a concentration of 1M.

51. The mixed metal compound of claim 44, wherein the starting material compound is treated with the acid, chelating agent or mixture thereof of for a period of 5 minutes or longer.

52. The mixed metal compound of claim 44 wherein the starting material compound is treated with the acid, chelating agent or mixture thereof of for a period of 15 minutes or longer.

53. The mixed metal compound of claim 44, wherein the starting material compound is treated with the acid, chelating agent or mixture thereof of for a period of 1 hour or longer.

54. The mixed metal compound of claim 44, wherein the starting material compound is treated with the acid, chelating agent or mixture thereof of for a period of 1 hour or less.

55. The mixed metal compound of claim 44, wherein the starting material compound is treated with the acid, chelating agent or mixture thereof of for a period of 30 minutes or less.

56. The mixed metal compound of claim 44, wherein the starting material compound is treated with the acid, chelating agent or mixture thereof of for a period of 15 minutes or less.

57. A process for the production of a phosphate binding bivalent metal-depleted mixed metal compound of formula (IV)

$$[M^{II}_{1-a}M^{III}_{a}O_{b}(OH)_{d}](A^{n-})_{c}\cdot zH_{2}O \qquad (IV)$$

wherein $0.98>a\geq 0.7$;
the process comprising the steps of:
a) contacting a starting material compound of formula (IV)

$$[M^{II}_{1-a}M^{III}_{a}O_{b}(OH)_{d}](A^{n-})_{c}\cdot zH_{2}O \qquad (IV)$$

wherein $0<a\leq 0.4$;
with an acid, a chelating agent, or a mixture thereof;
b) washing the contacted starting material until the mixed metal compound comprises less than 15% water soluble salts by weight of the mixed metal compound after drying; and
c) optionally subjecting the resulting compound to heat treatment;
wherein $M^{II}$ is at least one bivalent metal selected from the group consisting of Mg (II), Zn (II), Fe (II), Cu (II), Ca (II), La (II), Ce (II), and Ni(II);
$M^{III}$ is at least one trivalent metal selected from the group consisting of Mn(III), Fe(III), La(III), and Ce(III);
$A^{n-}$ is at least one n-valent anion and wherein at least one anion is carbonate;
$0\leq d\leq 2$;
the value of c for each anion is determined by the need for charge neutrality as expressed by the formula $2+a-2b-d-cn=0$;
$0\leq d\leq 2$;
$0<0\leq z\leq 5$.

58. A process for the production of a phosphate binding bivalent metal-depleted mixed metal compound of formula (IV)

$$[M^{II}_{1-a}M^{III}_{a}O_{b}(OH)_{d}](A^{n-})_{c}\cdot zH_{2}O \qquad (IV)$$

wherein $0.98>a\geq 0.7$;
the process comprising the steps of:
a) contacting a starting material compound of formula (IV)

$$[M^{II}_{1-a}M^{III}_{a}O_{b}(OH)_{d}](A^{n-})_{c}\cdot zH_{2}O \qquad (IV)$$

wherein $0<a\leq 0.4$;
with an acid, a chelating agent, or a mixture thereof; and
b) washing the contacted starting material until the mixed metal compound comprises less than 15% water soluble salts by weight of the mixed metal compound after drying; and
c) optionally subjecting the resulting compound to heat treatment;
wherein $M^{II}$ comprises Mg (II);
$M^{III}$ is at least one trivalent metal selected from the group consisting of Mn(III), Fe(III), La(III), and Ce(III);
$A^{n-}$ is at least one n-valent anion and wherein at least one anion is carbonate;
$0\leq d\leq 2$;
the value of c for each anion is determined by the need for charge neutrality as expressed by the formula $2+a-2b-d-cn=0$;
$0\leq d\leq 2$; and
$0<0\leq z\leq 5$.

59. The process of claim 58 wherein, the acid or chelating agent is selected from one or more members of the group consisting of HCl, $H_2SO_4$, Citric Acid, EDTA, $HNO_3$, and Acetic Acid.

60. The process of claim 58, wherein the acid or chelating agent is hydrochloric acid.

61. The process of claim 60, wherein the hydrochloric acid is at a concentration of in a range of 0.01 M to 5M.

62. The process of claim 60, wherein the hydrochloric acid is at a concentration of in a range of 0.1 M to 2 M.

63. The process of claim 60, wherein the hydrochloric acid is at a concentration of in a range of 0.5 M to 1.5 M.

64. The process of claim 60, wherein the hydrochloric acid is at a concentration of 1 M.

65. The process of claim 58, comprising contacting the starting material compound with the acid or the chelating agent for a period of 5 minutes or longer.

66. The process of claim 58, comprising contacting the starting material compound with the acid or the chelating agent for a period of 15 minutes or longer.

67. The process of claim 58, comprising contacting the starting material compound with the acid or the chelating agent for a period of a period of 1 hour or longer.

68. The process of claim 58, comprising subjecting the resulting compound to a heat treatment, wherein the heat treatment results in calcination.

69. A mixed metal compound prepared by a process as defined in claim 58.

70. A pharmaceutical composition comprising
   (a) a compound as defined in claim 23, and
   (b) a pharmaceutically acceptable carrier, diluent, excipient or adjuvant.

71. A method of binding phosphate in a subject, comprising administering to the subject a mixed metal compound as defined in claim 23.

72. A method for the treatment in a subject of any one of hyperphosphataemia, metabolic bone disease, metabolic syndrome, renal insufficiency, hypoparathyroidism, pseudohypoparathyroidism, acute untreated acromegaly, chronic kidney disease (CKD), severe hone problems, soft tissue calcification, secondary hyperparathyroidism, over medication of phosphate salts and other conditions requiring control of phosphate absorption, comprising administering a mixed metal compound as defined in claim 23.

73. The method of claim 72, comprising administering the mixed metal compound of claim 23 for the treatment of hyperphosphataemia.

74. The pharmaceutical composition of claim 1, wherein $0.98 > a \geq 0.8$.

75. The pharmaceutical composition of claim 1, wherein $M^{II}$ is Mg(II).

76. A pharmaceutical composition comprising a phosphate binding mixed metal compound according to formula (I)

$$M^{II}_{1-a}M^{III}_{a} \tag{I}$$

wherein $M^{II}$ is at least one bivalent metal, and the at least one bivalent metal comprises Mg(II);
$M^{III}$ is at least one trivalent metal; and
$0.98 > a \geq 0.7$;
the compound contains at least one n-valent anion $A^{n-}$ such that the compound is charge neutral, and the mixed metal compound comprises less than 15% water soluble salts by weight of the mixed metal compound after drying.

* * * * *